United States Patent [19]

Bodor

[11] Patent Number: 4,963,682

[45] Date of Patent: Oct. 16, 1990

[54] NOVEL RADIOPHARMACEUTICALS AND CHELATING AGENTS USEFUL IN THEIR PREPARATION

[75] Inventor: Nicholas S. Bodor, Gainesville, Fla.

[73] Assignee: University of Florida, Gainesville, Fla.

[21] Appl. No.: 89,009

[22] Filed: Aug. 21, 1987

Related U.S. Application Data

[63] Continuation of Ser. No. 850,299, Mar. 19, 1986, abandoned, which is a continuation-in-part of Ser. No. 632,383, Jul. 19, 1984, abandoned.

[51] Int. Cl.$^5$ .................. C07D 211/82; C07D 211/84; C07D 211/90; C07D 211/70
[52] U.S. Cl. ..................................... 546/338; 546/290; 546/294; 546/295; 546/296; 546/298; 546/299; 546/300; 546/314; 546/316; 546/318; 546/321; 546/323; 546/326; 546/328; 546/334; 546/335; 546/336; 424/1.1
[58] Field of Search ............... 546/338, 290, 316, 323, 546/339, 341, 345, 346, 348, 294, 295, 296, 298, 299, 300, 314, 318, 321, 326, 328, 334, 335; 424/1.1

[56] References Cited

U.S. PATENT DOCUMENTS 4,771,059 9/1988 Bodor .

Primary Examiner—John S. Maples
Attorney, Agent, or Firm—Mary Katherine Baumeister; Dennis P. Clarke

[57] ABSTRACT

A dihydropyridine⟷pyridinium salt type of redox, or chemical, delivery system for the site-specific and/or site-enhanced delivery of a radionuclide to the brain is provided. A chelating agent capable of chelating with a radionuclide and having a primary, secondary or tertiary amino function can be converted to the corresponding analogue in which said function is replaced with a dihydropyridine⟷pyridinium salt redox system and then complexed with a radionuclide to provide a new radiopharmaceutical that, in its lipoidal dihydropyridine form, penetrates the blood-brain barrier ("BBB") and allows increased levels of radionuclide concentration in the brain, particularly since oxidation of the dihydropyridine moiety in vivo to the ionic pyridinium salt retards elimination from the brain while elimination from the general circulation is accelerated.

This radionuclide delivery system is well suited for use in scintigraphy and similar radiographic techniques.

7 Claims, No Drawings

NOVEL RADIOPHARMACEUTICALS AND CHELATING AGENTS USEFUL IN THEIR PREPARATION

CROSS-REFERENCE TO RELATED APPLICATIONS

This application is a continuation of applicant's copending application Ser. No. 850,299, filed Mar. 19, 1986, now abandoned, which is a continuation-in-part of application Ser. No. 632,383, filed July 19, 1984, now abandoned. Copending application Ser. No. 850,299 is the U.S. national phase of International PCT Application No. PCT/US85/01333, filed July 15, 1985.

FIELD OF THE INVENTION

The present invention relates to a dihydropyridine⟷pyridinium salt type of redox, or chemical, delivery system for the site-specific and/or site-enhanced delivery of a radionuclide to the brain and other organs. More particularly, this invention relates to the discovery that a chelating agent capable of chelating with a radionuclide and having a primary, secondary or tertiary amino function can be converted to the corresponding analogue in which said function is replaced with a dihydropyridine⟷pyridinium salt redox system and then complexed with a radionuclide to provide a new radiopharmaceutical that, in its lipoidal dihydropyridine form, penetrates the blood-brain barrier ("BBB") and allows increased levels of radionuclide concentration in the brain, particularly since oxidation of the dihydropyridine moiety in vivo to the ionic pyridinium salt retards elimination from the brain while elimination from the general circulation is accelerated.

The present radionuclide delivery system is well suited for use in scintigraphy and similar radiographic techniques.

BACKGROUND OF THE INVENTION

Radiographic techniques such as scintigraphy, and the like, find application in biological and medical procedures for diagnosis as well as research. Scintigraphy involves the use of radiopharmaceuticals; i.e., compounds containing (or labeled with) a radioisotope (i.e. radionuclide) which upon introduction into a mammal become localized in specific organs, tissue, or skeletal material that are sought to be imaged. When the radiopharmaceutical is so localized, traces, plates, or scintiphotos of the existing distribution of the radionuclide may be made by various radiation -detectors known in the art. The observed distribution of the localized radionuclide can then be used to detect the presence of pathological conditions, abnormalities, and the like. Radiopharmaceuticals are thus often referred to as radiodiagnostics.

In many cases, radiopharmaceuticals are prepared using target-specific chelating agents which provide a bridge connecting a radionuclide, such as a radioactive metal like technetium-99m, or the like, and a material which will temporarily localize in the organ, tissue, or skeletal material which is to be imaged. Typical chelating agents for such purposes are: polydentate ligands that form a 1:1 or 2:1 ligand: radioactive metal complex; macrocyclic ligands of appropriate ring size and preferably where all coordinating atoms are in a planar configuration; and bicyclic or polycyclic ligands that can encapsulate the radioactive metal.

It is a well established fact that the delivery of drugs, including radiopharmaceuticals, to the brain is often seriously limited by transport and metabolism factors and, more specifically, by the functional barrier of the endothelial brain capillary wall deemed the blood-brain barrier or BBB. Site-specific delivery and/or sustained delivery of drugs to the brain are even more difficult.

A dihydropyridine⟷pyridinium redox system has now been successfully applied to delivery to the brain of a number of drugs. Generally speaking, according to this system, a dihydropyridine derivative of a biologically active compound is synthesized, which derivative can enter the CNS through the blood-brain barrier following its systemic administration. Subsequent oxidation of the dihydropyridine species to the corresponding pyridinium salt leads to delivery of the drug to the brain.

Two main approaches have been used thus far for delivering drugs to the brain using this redox system. The first approach involves derivation of selected drugs which contain a pyridinium nucleus as an integral structural component. This approach was first applied to delivering to the brain N-methylpyridinium-2-carbaldoxime chloride (2-PAM), the active nucleus of which constitutes a quaternary pyridinium salt, by way of the dihydropyridine latentiated prodrug form thereof. Thus, a hydrophilic compound (2-PAM) was made lipoidal (i.e. lipophilic) by making its dihydropyridine form (Pro-2-PAM) to enable its penetration through lipoidal barriers. This simple prodrug approach allowed the compound to get into the brain as well as other organs, but this manipulation did not and could not result in any brain specificity. On the contrary, such approach was delimited to relatively small molecule quaternary pyridinium ring-containing drug species and did not provide the overall ideal result of brain-specific, sustained release of the desired drug, with concomitant rapid elimination from the general circulation, enhanced drug efficacy and decreased toxicity. No "trapping" in the brain of the 2-PAM formed in situ resulted, and obviously no brain-specific, sustained delivery occurred as any consequence thereof: the 2-PAM was eliminated as fast from the brain as it was from the general circulation and other organs. Compare U.S. Pat. Nos. 3,929,813 and 3,962,447; Bodor et al, *J. Pharm. Sci.*, 67, No. 5, pp. 685–687 (1978); Bodor et al, *Science*, Vol. 190 (1975), pp. 155–156; Shek, Higuchi and Bodor, *J. Med. Chem.*, Vol. 19 (1976), pp. 113–117. A more recent extension of this approach is described by Brewster, *Dissertation Abstracts International*, Vol. 43, No. 09, March 1983, p. 2910B. See also Bodor et al, *Science*, Vol. 214, Dec. 18, 1981, pp. 1370–1372.

The second approach for delivering drugs to the brain using the redox system involves the use of a pyridinium carrier chemically linked to a biologically active compound. Bodor et al, *Science*, Vol. 214, Dec. 18, 1981, pp. 1370–1372, outlines a scheme for this specific and sustained delivery of drug species to the brain, as depicted in the following Scheme A:

SCHEME A: BBB, BLOOD-BRAIN BARRIER

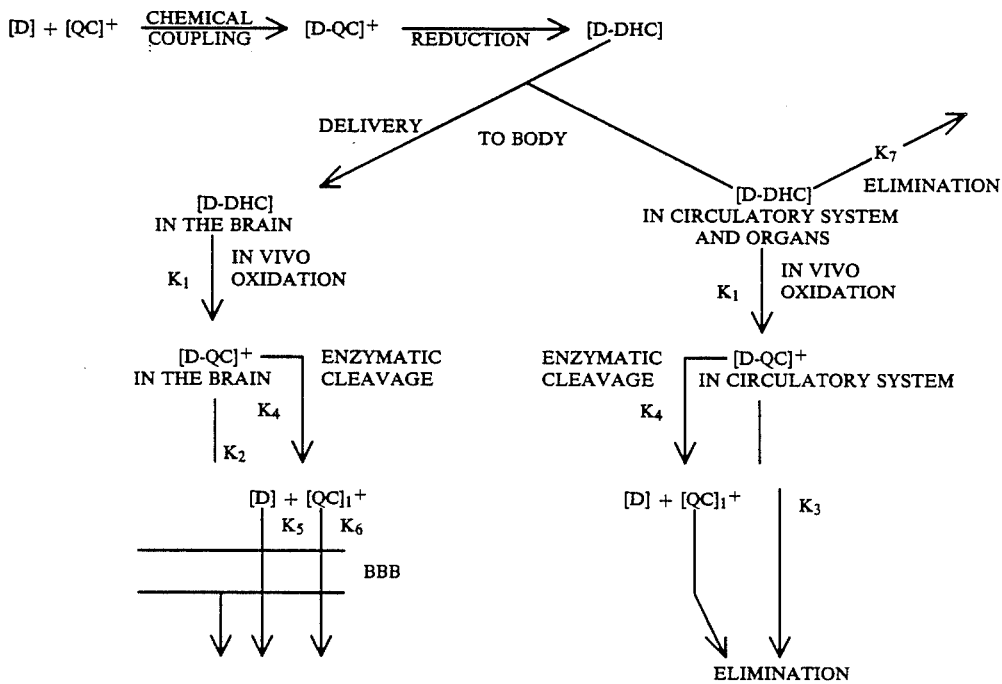

According to the scheme in *Science*, a drug [D] is coupled to a quaternary carrier [QC]+ and the [D-QC]+ which results is then reduced chemically to the lipoidal dihydro form [D-DHC]. After administration of [D-DHC] in vivo, it is rapidly distributed throughout the body, including the brain. The dihydro form [D-DHC] is then in situ oxidized (rate constant, $k_1$) (by the NAD$\leftrightarrow$NADH system) to the ideally inactive original [D-QC]+ quaternary salt which, because of its ionic, hydrophilic character, should be rapidly eliminated from the general circulation of the body, while the blood-brain barrier should prevent its elimination from the brain ($k_3 \gg k_2$; $k_3 \gg k_7$). Enzymatic cleavage of the [D-QC]+ that is "locked" in the brain effects a sustained delivery of the drug species [D], followed by its normal elimination ($k_5$), metabolism. A properly selected carrier [QC]+ will also be rapidly eliminated from the brain ($k_6 > k_2$). Because of the facile elimination of [D-QC]+ from the general circulation, only minor amounts of drug are released in the body ($k_3 \gg k_4$); [D] will be released primarily in the brain ($k_4 > k_2$). The overall result ideally will be a brain-specific sustained release of the target drug species. Specifically, Bodor et al worked with phenylethylamine as the drug model. That compound was coupled to nicotinic acid, then quaternized to give compounds of the formula

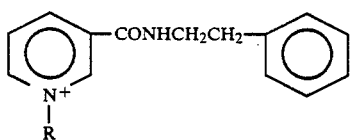

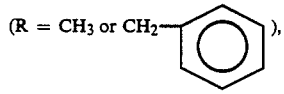

($R = CH_3$ or $CH_2-\!\!\bigcirc$ ), which were subsequently reduced by sodium dithionite to the corresponding compounds of the formula

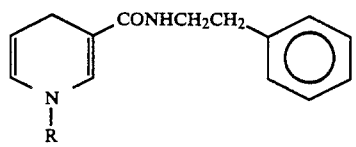

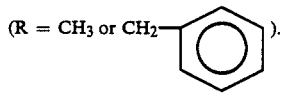

($R = CH_3$ or $CH_2-\!\!\bigcirc$ ).

Testing of the N-methyl derivative in vivo supported the criteria set forth in Scheme A. Bodor et al speculated that various types of drugs might possibly be delivered using the depicted or analogous carrier systems and indicated that use of N-methylnicotinic acid esters and amides and their pyridine ring-substituted derivatives was being studied for delivery of amino- or hydroxyl-containing drugs, including small peptides, to the brain. No other possible specific carriers were disclosed. Other reports of this work with the redox carrier system have appeared in *The Friday Evening Post*, Aug. 14, 1981, Health Center Communciations, University of Florida, Gainesville, Fla.; *Chemical & Engineering News*, Dec. 21, 1981, pp. 24–25; and *Science News*, Jan. 2, 1982, Vol. 121, No. 1, page 7. More recently, the present inventor has substantially extended the redox carrier system in terms of possible carriers and drugs to be delivered; see, for example International Patent Application No. PCT/US83/00725, filed by UNIVERSITY OF FLORIDA on May 12, 1983 and published under International Publication No. WO83/03968 on Nov. 4, 1983.

Nevertheless, serious need also has existed in this art for new, centrally acting drugs which can be site-specifically and sustainedly delivered to the brain, while at the same time avoiding the aforesaid noted and notable disadvantages and drawbacks associated with penetration of the blood-brain barrier, with dihydropyridine latentiated prodrug forms of drug species themselves comprising a pyridinium salt active nucleus, with the necessity for introducing critically coordinated and designed, release rate-controlling substituents onto any particular drug carrier moiety, and/or with the limitation of delivery of only known drug entities. This need has led to a new approach for delivering drugs to the brain using the redox system. This novel approach provides new derivatives of centrally acting amines in which a primary, secondary or tertiary amino function has been replaced with a dihydropyridine/pyridinum salt redox system. These new dihydropyridine analogues are characterized by the structural formula

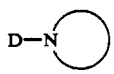

wherein D is the residue of a centrally acting primary, secondary or tertiary amine, and

is a radical of the formula

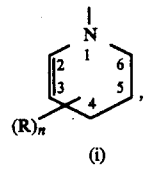
(i)

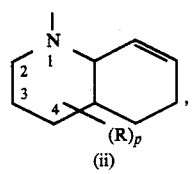
(ii)

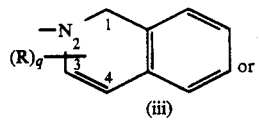
(iii) or

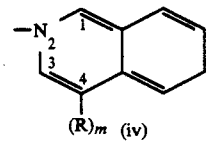
(iv)

wherein the dotted line in formula (i) indicates the presence of a double bond in either the 4 or 5 position of the dihydropyridine ring; the dotted line in formula (ii) indicates the presence of a double bond in either the 2 or 3 position of the dihydroquinoline ring system; m is zero or one; n is zero, one or two; p is zero, one or two, provided that when p is one or two, each R in formula (ii) can be located on either of the two fused rings; q is zero, one, or two, provided that when q is one or two, each R in formula (iii) can be located on either of the two fused rings; and each R is independently selected from the group consisting of halo, $C_1$–$C_7$ alkyl, $C_1$–$C_7$ alkoxy, $C_2$–$C_8$ alkoxycarbonyl, $C_2$–$C_8$ alkanoyloxy, $C_1$–$C_7$ haloalkyl, $C_1$–$C_7$ alkylthio, $C_1$–$C_7$ alkylsulfinyl, $C_1$–$C_7$ alkylsulfonyl, CH=NOR''' wherein R''' is H or $C_1$–$C_7$ alkyl, and —CONR'R'' wherein R' and R'', which can be the same or different, are each H or $C_1$–$C_7$ alkyl.

The new dihydropyridine analogues described in the preceding paragraph act as a delivery system for the corresponding quaternary compounds in vivo; the quaternary derivatives, which also are chemical intermediates to the dihydro compounds, are pharmacologically active and are characterized by site-specific and sustained delivery to the brain when administered via the corresponding dihydropyridine form. Nevertheless, a serious need still exists for an effective genera method for the site-specific and/or sustained delivery of a desired radionuclide to the brain. It would therefore be desirable to adapt the analogue concept to the radiopharmaceutical area.

Summary of the Invention

It has now been found that a chemical delivery system based upon a dihydropyridine⇌pyridinium salt type redox system is uniquely well suited for an effective site-specific and/or sustained and/or enhanced delivery of a radionuclide to the brain or like organ, via novel redox system-containing radiopharmaceuticals, and novel redox system-containing chelating agents and novel redox system-containing precursors thereto, useful in the preparation of said radiopharmaceuticals. In one aspect, the present invention thus provides novel redox system-containing chelating agent precursors having the formula

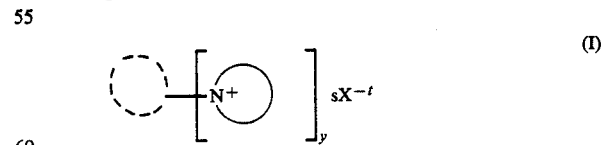
(I)

wherein is the residue of a chelating agent capable of chelating with a metallic radionuclide, said chelating agent having at least one primary, secondary or tertiary amino functional group, said functional group being not essential for the complexing properties of said chelating agent, said residue being characterized by the absence of at least one of said primary, secondary or tertiary amino functional groups from the chelating agent; y is 1 or 2;

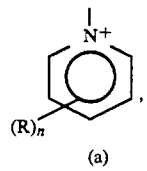

is a radical of the formula

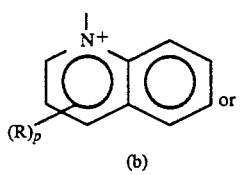
(a)

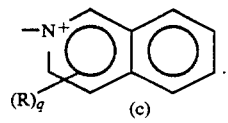
(b)

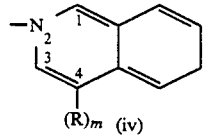
(c)

wherein n is zero, one or two; p is zero, one or two provided that when p is one or two, each R in formula (b) can be located on either of the two fused rings; q is zero, one, or two, provided that when q is one or two, each R in formula (c) can be located on either of the two fused rings; and each R is independently selected from the group consisting of halo, $C_1-C_7$ alkyl, $C_1-C_7$ alkoxy, $C_2-C_8$ alkoxycarbonyl, $C_2-C_8$ alkanoyloxy, $C_1-C_7$ haloalkyl, $C_1-C_7$ alkylthio, $C_1-C_7$ alkylsulfinyl, $C_1-C_7$ alkylsufonyl, —CH=NOR''' wherein R''' is H or $C_1-C_7$ alkyl, and -CONR'R'' wherein R' and R'', which can be the same or different, are each H or $C_1-C_7$ alkyl; $X^-$ is the anion of a pharmaceutically acceptable organic or inorganic acid; t is the valence of the acid anion; and s is a number which when multiplied by t is equal to y.

In another aspect, the present invention provides novel redox system-containing chelating agents having the formula

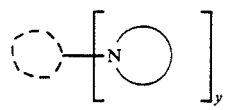
(II)

and the non-toxic pharmaceutically acceptable salts thereof, wherein

and y are defined as above, and

is a radical of the formula

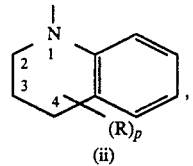
(i)

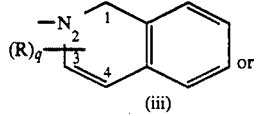
(ii)

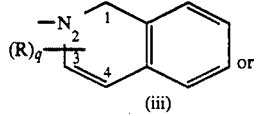
(iii)

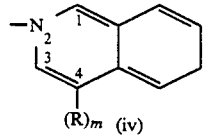
(iv)

wherein the dotted line in formula (i) indicates the presence of a double bond in either the 4 or 5 position of the dihydropyridine ring; the dotted line in formula (ii) indicates the presence of a double bond in either the 2 or 3 position of the dihydroquinoline ring system; m is zero or one; n is zero, one or two; p is zero, one or two, provided that when p is one or two, each R in formula (ii) can be located on either of the two fused rings; q is zero, one, or two, provided that when q is one or two, each R in formula (iii) can be located on either of the two fused rings; and each R is independently selected from the group consisting of halo, $C_1-C_7$ alkyl, $C_1-C_7$ alkoxy, $C_2-C_8$ alkoxycarbonyl, $C_2-C_8$ alkanoyloxy, $C_1-C_7$ haloalkyl, $C_1-C_7$ alkylthio, $C_1-C_7$ alkylsulfinyl, $C_1-C_7$ alkylsufonyl, —CH=NOR''' wherein R'''is H or $C_1-C_7$ alkyl, and —CONR'R'' wherein R' and R'', which can be the same or different, are each H or $C_1-C_7$ alkyl.

In yet another aspect, the present invention provides, as an effective radionuclide delivery system, novel redox system-containing radiopharmaceuticals of the formula

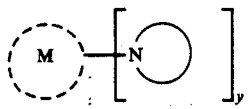

(III)

and the non-toxic pharmaceutically acceptable salts thereof, wherein M is a metallic radionuclide and the remaining structural variables are defined as before; in other words, (III) is the chelated, or complexed, counterpart of (II), formed by complexing the novel redox system-containing chelating agent of formula (II) with a radioactive metal. When a radiopharmaceutical of formula (III) is administered, due to its lipoidal nature it readily penetrates the BBB. Oxidation of (III) in vivo affords the corresponding pyridinium salt of the formula

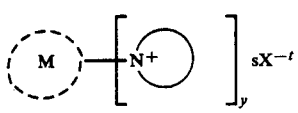

(IV)

wherein the structural variables are as defined above. Because of its hydrophilic, ionic nature, the formula (IV) substance is "locked-in" the brain, thus allowing radiographic imaging of the radionuclide present in the complex (IV). There is no readily biologically cleavable bond between the redox portion of the formula (IV) complex and the radiolabeled chelate portion thereof. Consequently, it is not expected that the quaternary "locked in" form will gradually cleave to release the redox moiety and the chelate portion of the molecule. Rather, sustained levels of the formula (IV) quaternary will be present at the desired site.

It is generally considered most desirable, from the standpoint of patient and technician safety, to image the target area as soon as possible after administration and to use relatively short-lived radioisotopes. Under these circumstances, or indeed even when longer lived radioisotopes are utilized, the "locked-in" quaternary form is not expected to be metabolized or to exit the brain until after the radioactivity has decayed to a considerable extent. Thus, the present invention does not in fact provide a system for delivery and imaging of previously known radiopharmaceuticals; by the time the present delivery system would no longer be in its "locked in" quaternary form, it would generally no longer be sufficiently radioactive for practical imaging. Thus, in contrast to the teachings of the Bodor et al publications. e.g. Bodor et al. *Science*, Vol. 214, Dec. 18, 1981. pp. 1370–1372, which emphasize the desirability of an inactive quaternary form locked in the brain, the present invention provides, and indeed requires, an active quaternary form locked in the brain in order to allow effective radionuclide imaging.

Technetium-99m is a preferred radionuclide for diagnostic purposes because of its favorable radiation energy, its relatively short half-life, and the absence of corpuscular radiation, and is preferred for use in the present invention. Other radionuclides that can be used diagnostically herein in a chelated form are cobalt-57, gallium-67, gallium-68, indium-111, indium-111m, and the like.

DETAILED DESCRIPTION OF THE INVENTION

The following definitions are applicable:

The term "drug" as used herein means any substance intended for use in the diagnosis, cure, mitigation, treatment or prevention of disease in man or other animal.

The expression "non-toxic pharmaceutically acceptable salts" as used herein generally includes the non-toxic salts of products of the invention of structures (II) and (III) hereinabove formed with non-toxic, pharmaceutically acceptable inorganic or organic acids of the general formula HX. For example, the salts include those derived from inorganic acids such as hydrochloric, hydrobromic, sulfuric, sulfamic, phosphoric, nitric and the like; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, fumaric, methanesulfonic, toluenesulfonic and the like. The expression "anion of a pharmaceutically acceptable organic or inorganic acid" as used herein, e.g. in connection with structures (I) and (IV) above, is intended to include anions of such HX acids.

The term "halo" encompasses fluoro, chloro, bromo and iodo.

The term "$C_1$–$C_7$ alkyl" includes straight and branched lower alkyl radicals having up to seven carbon atoms. When R, R', R" and/or R''' are $C_1$–$C_7$ alkyl, they are preferably methyl or ethyl.

The term "$C_1$–$C_7$ alkoxy" includes straight and branched chain lower alkoxy radicals having up to seven carbon atoms. When R is $C_1$–$C_7$ alkoxy, it is preferably methoxy or ethoxy.

The term "$C_2$–$C_8$ alkoxycarbonyl" designates straight and branched chain radicals of the formula

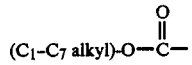

wherein the $C_1$–$C_7$ alkyl group is defined as above. When R is alkoxycarbonyl, it is preferably ethoxycarbonyl or isopropoxycarbonyl.

The term "$C_2$–$C_8$ alkanoyloxy" designates straight and branched chain radicals of the formula

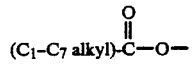

wherein the $C_1$–$C_7$ alkyl group is defined as above. When R is alkanoyloxy, it is preferably acetoxy, pivalyloxy or isobutyryloxy.

The term "$C_1$–$C_7$ haloalkyl" designates straight and branched chain lower alkyl radicals having up to seven carbon atoms and bearing one or more halo substituents (F, Cl, Br or I), which can be the same or different. Preferably, when R is haloalkyl, the group contains 1 or 2 carbon atoms and bears 1 to 3 halogen substituents, e.g. chloromethyl or trifluoromethyl.

The term "$C_1$–$C_7$ alkylthio" includes straight and branched chain radicals of the type

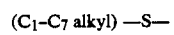

wherein $C_1$–$C_7$ alkyl is defined as before. When R is alkylthio, it is preferably methylthio.

The terms "$C_1-C_7$ alkylsulfinyl" and "$C_1-C_7$ alkylsulfonyl" designate radicals of the formulas ($C_1-C_7$ alkyl) —SO— and ($C_1-C_7$ alkyl) —SO$_2$—, respectively, wherein $C_1-C_7$ alkyl is defined as before. When R is alkylsulfinyl or alkylsulfonyl, methylsulfinyl and methylsulfonyl are preferred.

When R is —CH=NOR''', it is preferably —CH=NOH or CH=NOCH$_3$. When R is —CONR'R'', it is preferably —CONH$_2$ or —CON(CH$_3$)$_2$.

In formulas (I) through (IV) hereinabove, y is preferably 1; n, m, p or q is preferably one; and R is preferably located in the 3-position in structures (a), (b), (i) or (ii) and in the 4-position in structures (c) or (iii). R is preferably —CH=NOR''' or —CONR'R'' wherein R', R'' and R''' are as broadly defined hereinabove. Most preferably, R is —CONH$_2$ or CH=NOCH$_3$.

The expression "residue of a chelating agent capable of chelating with a metallic radionuclide, said chelating agent having at least one primary, secondary or tertiary amino functional group, said functional group being not essential for the complexing properties of said chelating agent, said residue being characterized by the absence of at least one of said primary, secondary or tertiary amino functional groups from the chelating agent" is believed to be self-explanatory. By way of example, if a chelating agent having a primary amino function which is non-essential in terms of chelating ability can be represented by the structural formula

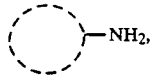

then the corresponding residue could be depicted as

in formulas (I) through (IV), the ring nitrogen atoms in structures (a) through (c) and (i) through (iv) are thus located in the same position as was the nitrogen atom of the original amino function. As a specific example, in the case of a chelating agent have the structure

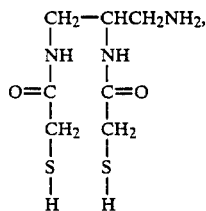

the corresponding residue would be

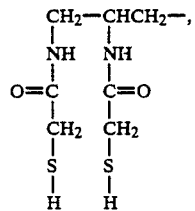

and the corresponding redox system-containing chelating agent precursor of formula (I) would have the structure

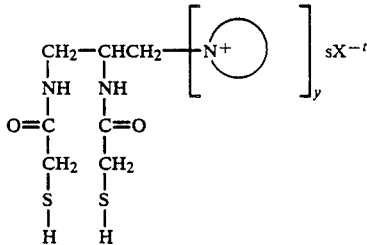

wherein y=1 and

s, X⁻ and t are defined as with formula (I). Similarly, when the chelating agent has the structure

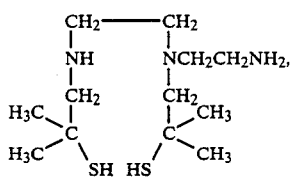

then the corresponding residue is

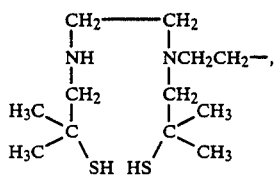

and the corresponding redox system-containing chelating agent precursor of formula (I) would have the structure

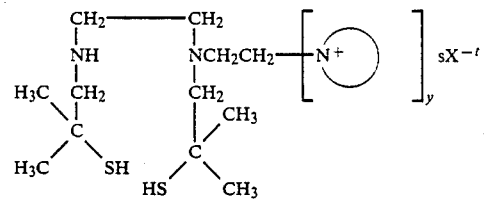

wherein y=1 and the other structural variables are defined as with formula (I).

As another example, when the chelating agent has the structure

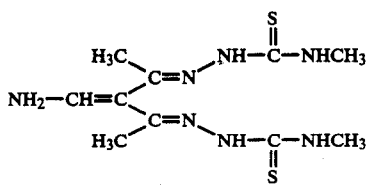

or

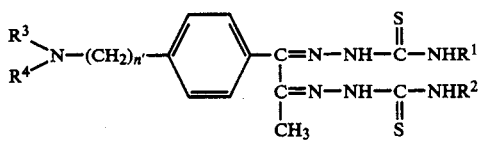

wherein $R^1$, $R^2$, $R^3$ and $R^4$ are each H or $C_1$-$C_3$ alkyl and n' is an integer of 0 to 3, then the corresponding residue is

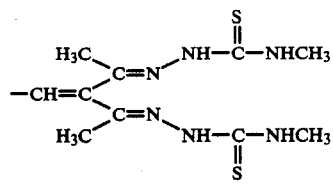

or

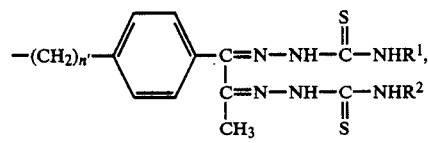

respectively; and the corresponding redox system-containing chelating agent precursor of formula (I) would have the structure

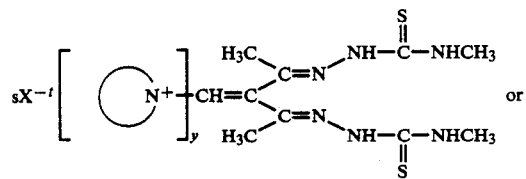

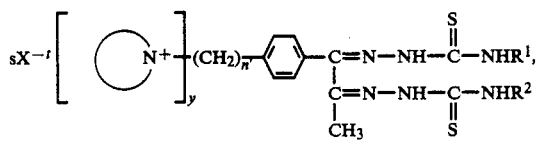

respectively, wherein y=1 and s, $X^-$ and t are as defined with formula (I) and $R^1$, $R^2$ and n' are as defined immediately above.

It will be apparent from the foregoing that the exact structure of the amino function in the chelating agents is immaterial insofar as concerns the structure of the instant derivatives of formulas (I) through (IV), for in formulas (I) through (IV) the entire amino function in the parent chelating agents has been replaced with a dihydropyridine/pyridinium salt redox system. Thus, virtually any chelating agent capable of complexing with a radionuclide and having at least one primary, secondary or tertiary amine functional group which is non-essential in terms of chelating properties can provide the chelating agents residue

in the instant derivatives. Many illustrative such amine groups will be apparent to those skilled in the art; most commonly, however, the chelating agent's functional group which is to be replaced with the redox system is simply an —$NH_2$ group. And such amino group can be readily introduced into the structure of a known chelating agent not already comprising same and then replaced by the instant redox system to give the desired derivatives, as described in more detail hereinbelow.

It too will be appreciated that the radical represented by

in formulas (II) and (III) must enable the complex of formula (III) to penetrate the BBB and must also be capable of being oxidized in vivo to the corresponding quaternary structure. The ionic entity which results from such in vivo oxidation is prevented from efflux from the brain, while elimination from the general circulation is accelerated. In contradistinction to the drug-carrier entities disclosed, for example, in Science, Vol. 214, Dec. 18, 1981, pp. 1370–1372, however, there is no readily metabolically cleavable bond between drug and quaternary portions; the active species delivered in the present case is the formula (IV) quaternary itself.

It will also be appreciated that a compound of formula (III) may be administered as the free base or in the form of a non-toxic pharmaceutically acceptable salt thereof, i.e. a salt which can be represented by the formula

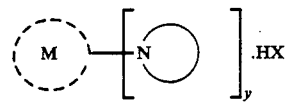

wherein M,

y and HX are defined as before; and that, regardless of the actual form in which the compound is administered, it will be converted in vivo to a quaternary salt of formula (IV), the anion $X^-$ being present in vivo. It is not necessary that the anion be introduced as part of the compound administered. Indeed, even when the compound of formula (III) is used in its salt form, the anion of the formula (IV) compound is not necessarily the same as that present in the formula (III) compound. Indeed, the exact identity of the anionic portion of the compound of formula (IV) is immaterial to the in vivo transformation of (III) to (IV).

Insofar as concerns the expression "said functional group being not essential for the complexing properties of said chelating agent", it will be apparent that this expression is intended to mean that any primary, secondary or tertiary amino functional group in a chelating agent which can be replaced with the instant redox system without destroying the chelating agent's ability to complex with the radionuclide is considered herein to be not essential for complexing properties. On the other hand, replacement of an amino functional group which would lead to a redox system-containing structure which would be incapable of complexing with a radionuclide is not within the ambit of this invention.

In accord with the present invention, the sustained delivery of a radionuclide to the brain in sufficient concentrations for radioimaging can be effected with much lower concentrations in the peripheral circulation and other tissues. The present invention of course will allow such imaging of any other organs or glands in which sufficient radioactivity accumulates. Thus, for example, it is expected that the quaternary form (IV) which is locked in the brain will be locked in the testes as well.

The novel radionuclide delivery system of this invention begins with the preparation of the novel redox system-containing chelating agent precursors of formula (I). The preparation of those precursors will be tailored to the particular chelating portion and redox portion to be combined, as well as to the presence or absence of other reactive functional groups (amino, mercapto, carboxyl, hydroxy) in either the chelating or redox portion. Typically, if such other reactive groups are present, they are found in the chelating portion. In any event, when such groups are present and it is desired to protect them, a step that introduces appropriate protecting groups can be incorporated at a suitable stage of the synthetic pathway. Protective groups are well known in the art and include t-butoxycarbonyl for amino groups, N-methyleneacetamido for mercaptans, and N-hydroxysuccinimidyl for carboxyl groups. Acyl or carbonate groups are typically utilized to protect alcohol hydroxyls. When carbonate protecting groups are desired, the step of introducing the protecting groups will involve reacting the alcohol with a halocarbonate of the type ROCOCl or ROCOBr (formed by reaction of ROH with COCl$_2$ or COBR$_2$), R typically being lower alkyl. For acyl protecting groups, the alcoholic hydroxyl is reacted with an acyl halide R'Cl or R'Br, R' being —COCH$_3$ or —COC(CH$_3$)$_3$. Yet other reaction schemes and reactants will be readily apparent to those skilled in the art as will the appropriate means for removing such protective groups after they have achieved their function and are no longer needed.

In forming the precursors of formula (I), at least one primary, secondary or tertiary amino functional group in a chelating agent will be replaced with

the hydrophilic, ionic pyridinium salt form of the dihydropyridine⇌pyridinium salt redox system.

It will be appreciated that by

there is intended any non-toxic redox moiety of structure (a), (b) or (c) hereinabove comprising, containing or including the pyridinium nucleus, whether or not a part of any larger basic nucleus, and whether substituted or unsubstituted, the only criterion therefor being capacity for chemical to the corresponding dihydropyridine form

BBB-penetration of

and in vivo oxidation of

back to the quaternary pyridinium salt redox moiety

As aforesaid, the ionic pyridinium salt radiopharmaceutical/redox entity of formula (IV) which results from in vivo oxidation of the dihydropyridine form (III) is prevented from efflux from the brain, while elimination from the general circulation is accelerated. Radioimaging of the radionuclide present in the "locked in" formula (IV) quaternary allows observation of the distribution of the localized radionuclide for diagnosis of pathological conditions, abnormalities, etc.

The following synthetic schemes illustrate various approaches to the preparation of the redox system-containing chelating agent precursors of formula (1), to the corresponding redox system-containing chelating agents of formula (II) and to the corresponding redox system-containing radiopharmaceuticals of formula (III). Also shown are the corresponding "locked in" quaternaries of formula (IV) formed by in vivo oxidation of the formula (III) chelates, said formula (IV) quaternaries being the primary localized materials whose radionuclide content is imaged by radiation detection means.

SCHEME 1
PART A:
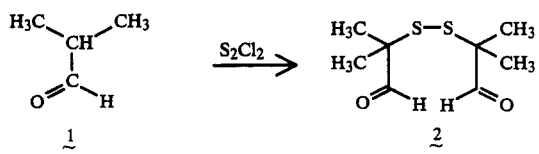
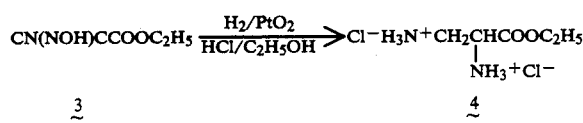
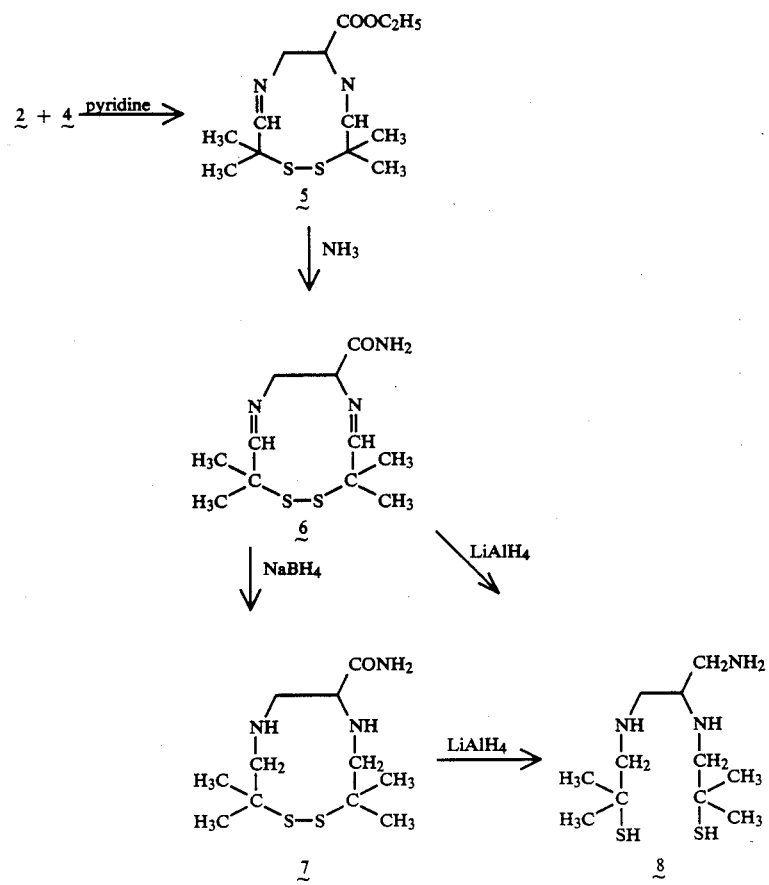
PART B, version 1:

-continued
SCHEME 1
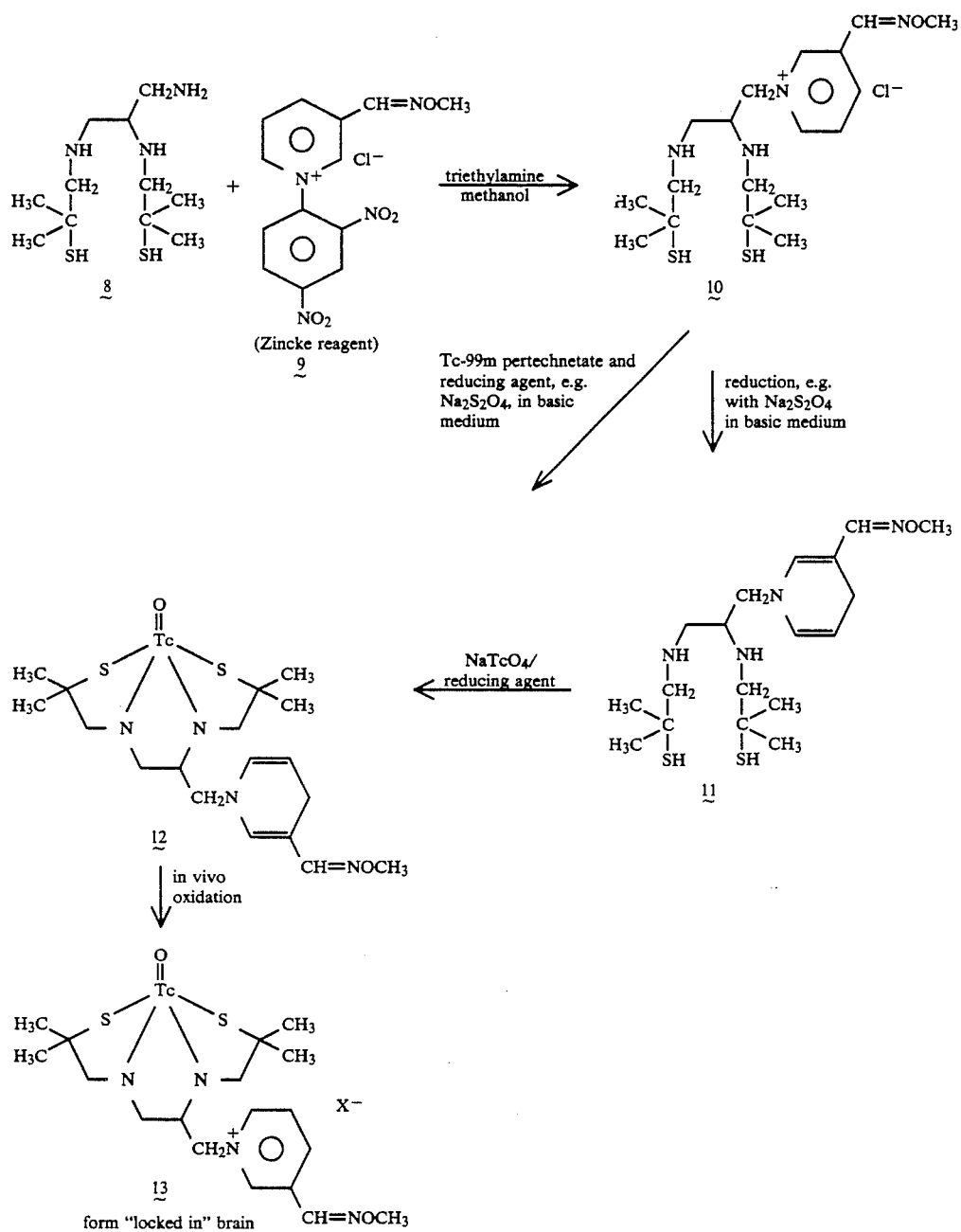
PART B, version 2:
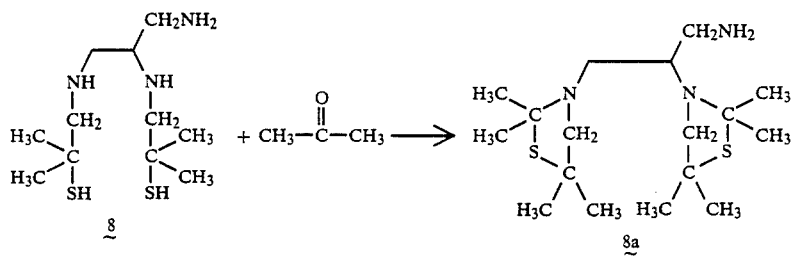

-continued
SCHEME 1
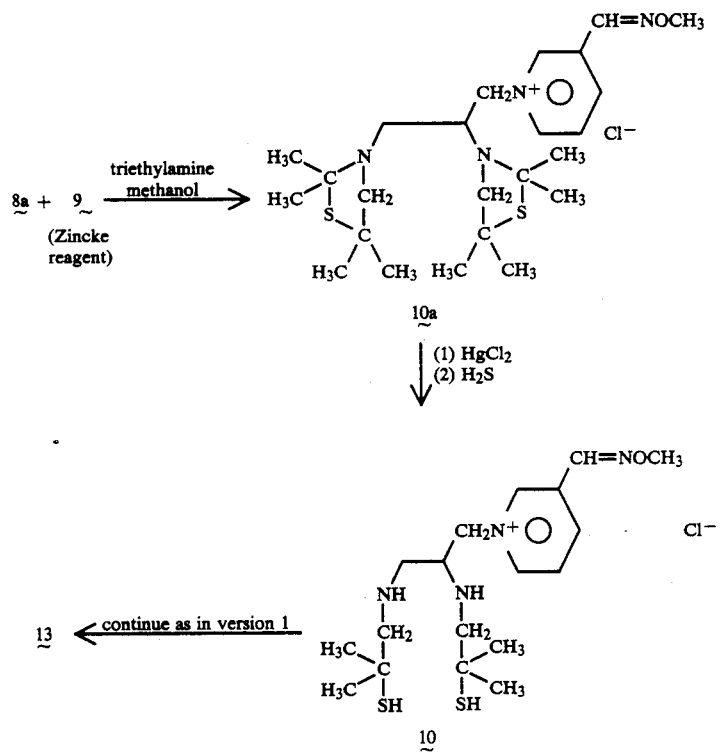
PART B, version 3:
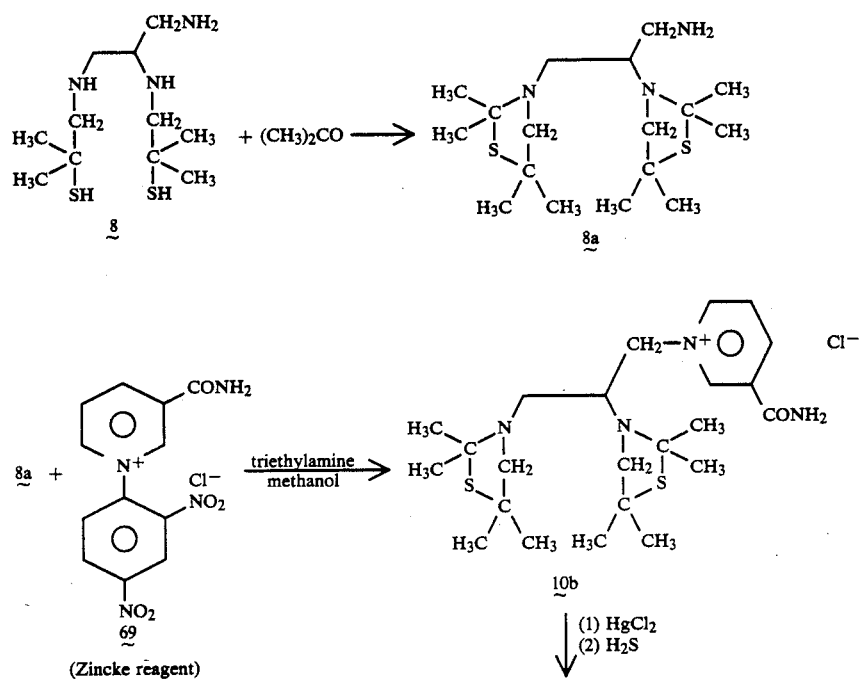

4,963,682
23
-continued
SCHEME 1
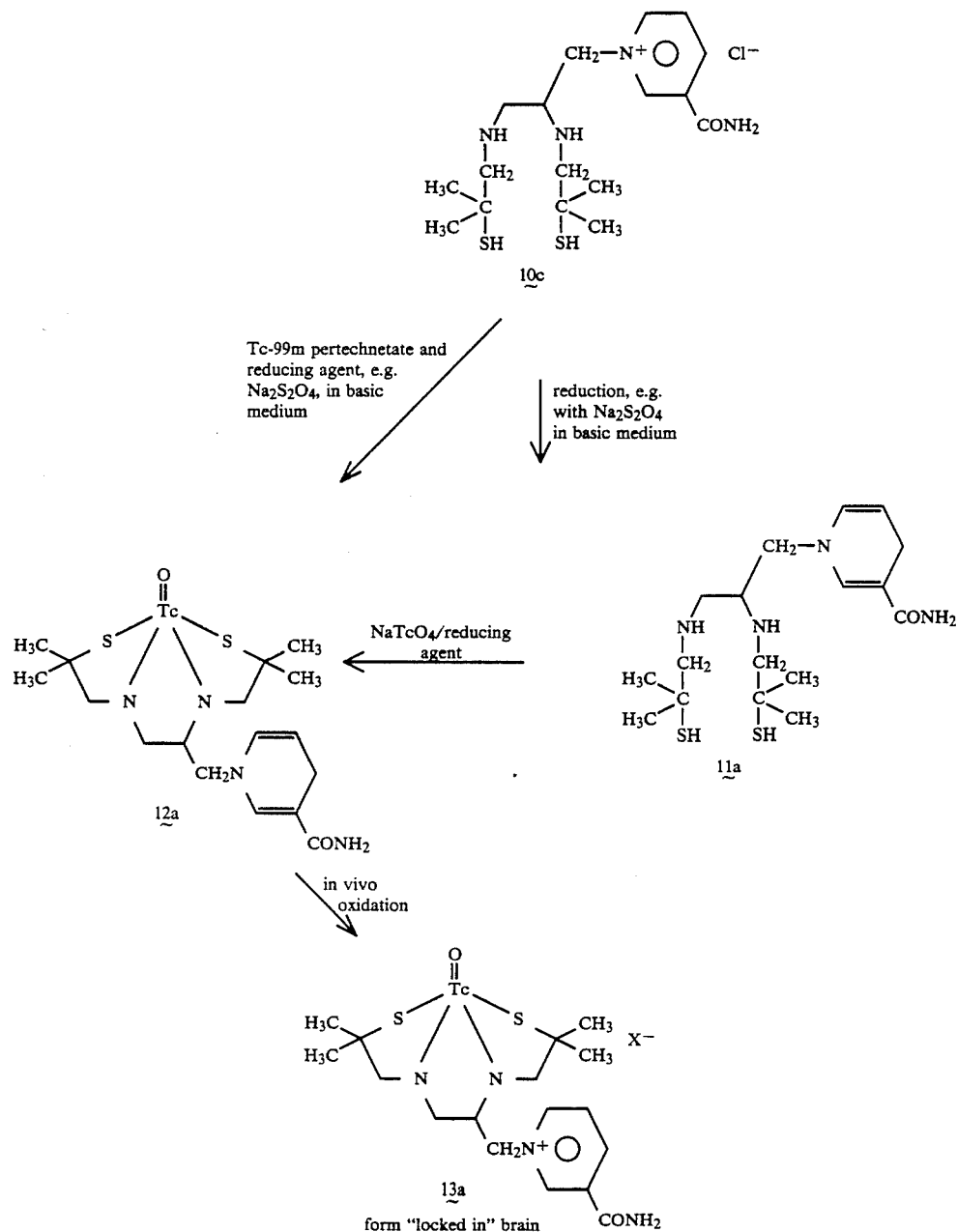
form "locked in" brain
SCHEME 2
PART A:
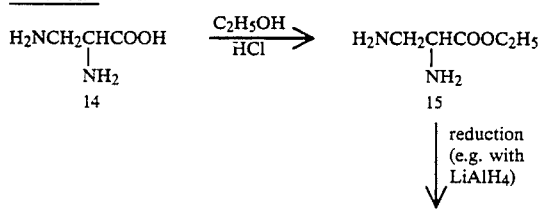
reduction
(e.g. with
LiAlH₄)

SCHEME 2
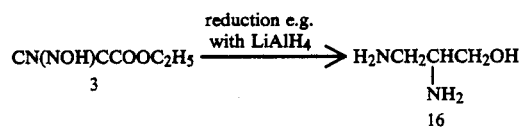
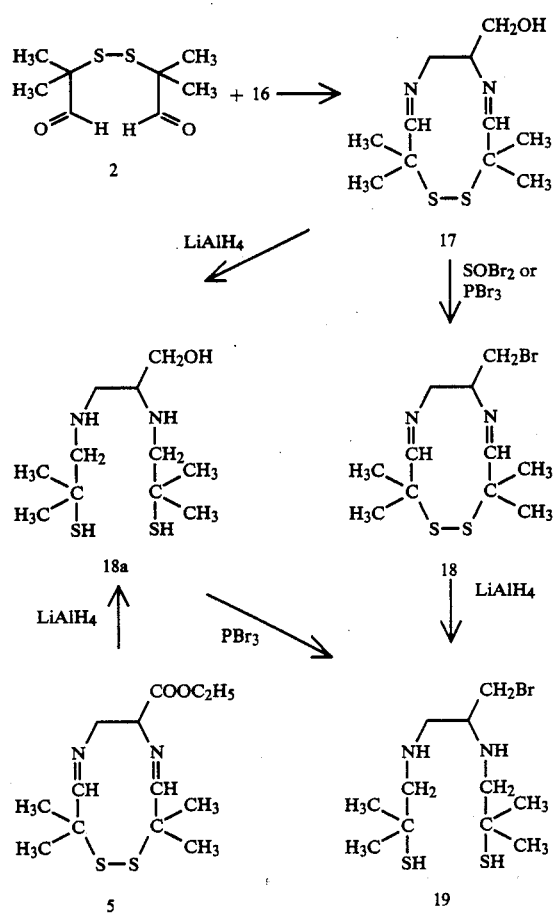
PART B, version 1:
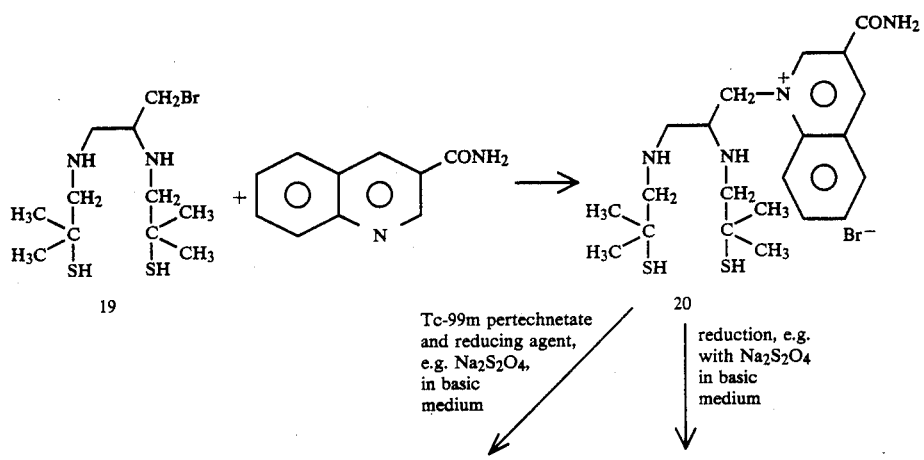

-continued
SCHEME 2
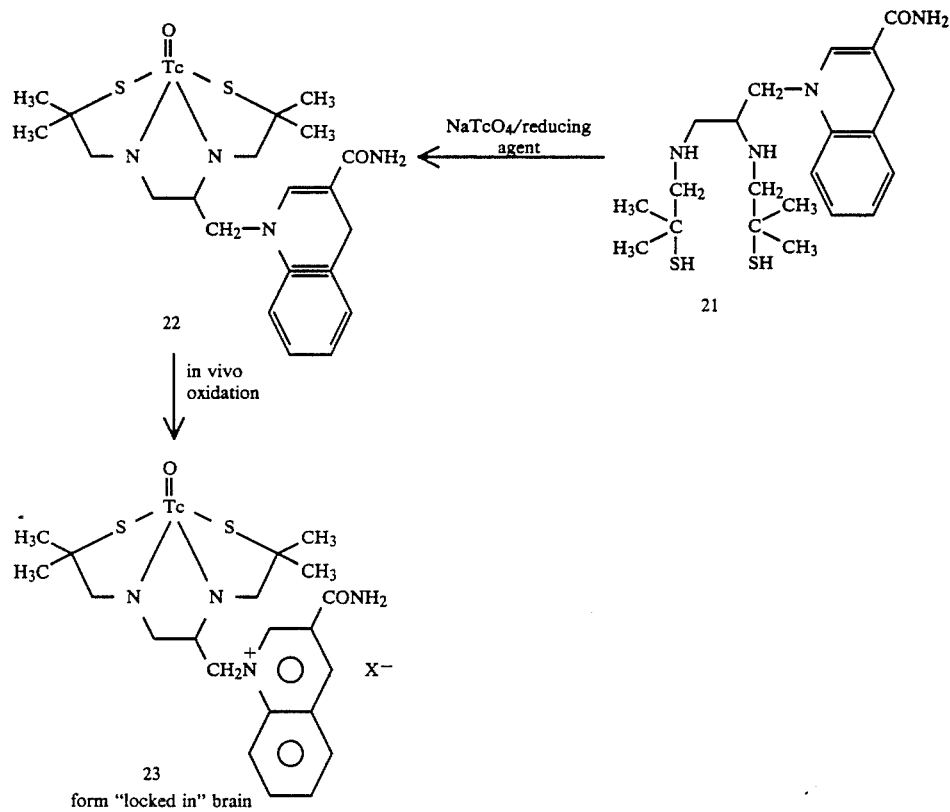
PART B, version 2:
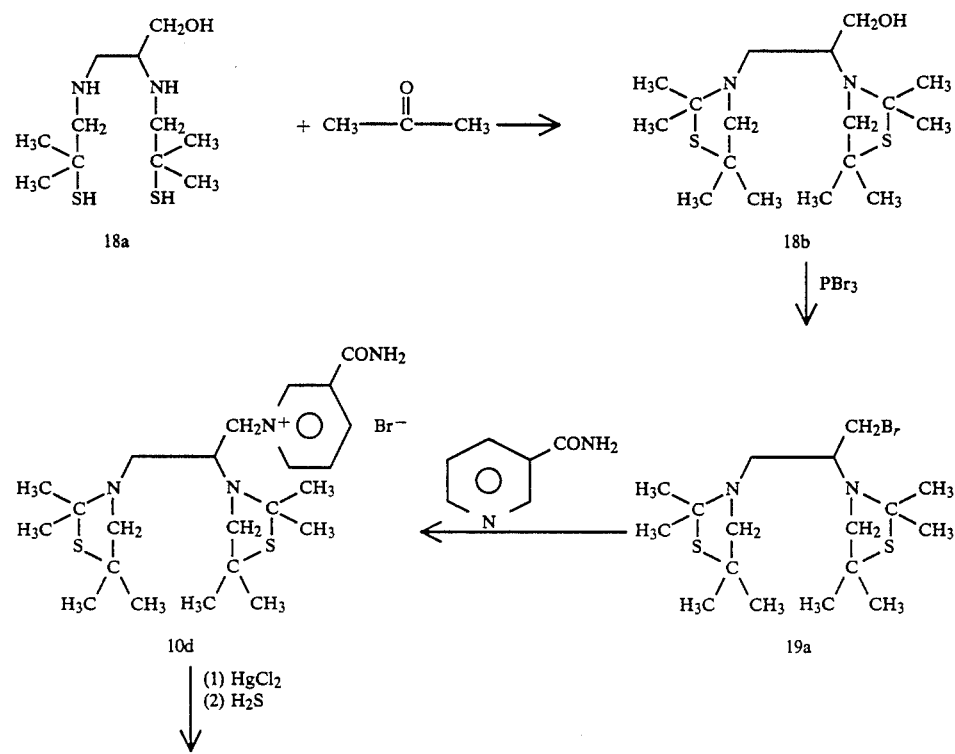

-continued
SCHEME 2
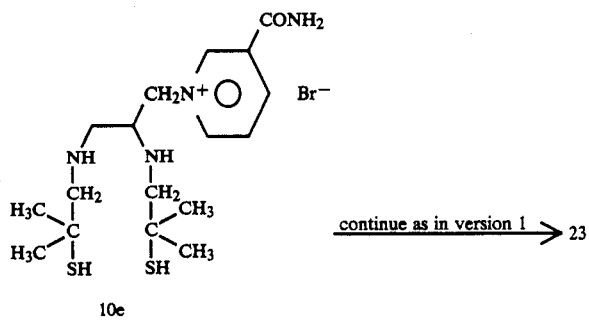
SCHEME 3
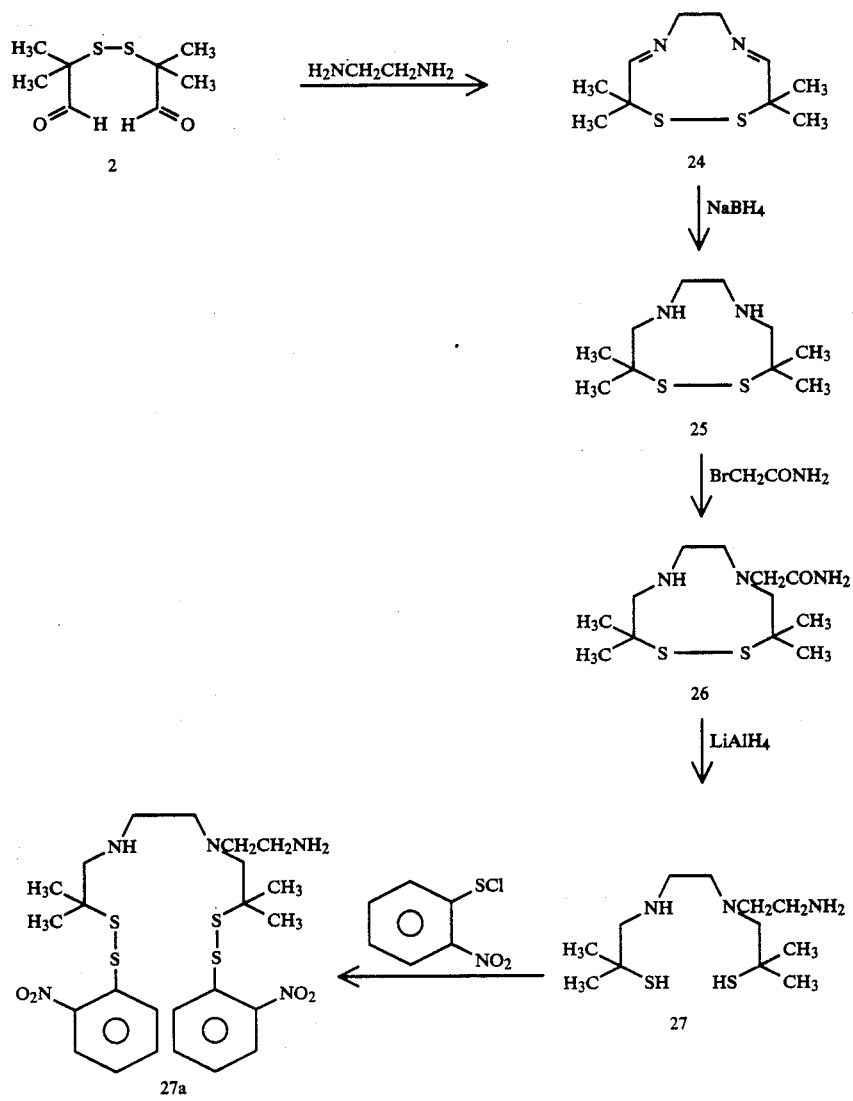

-continued
SCHEME 3
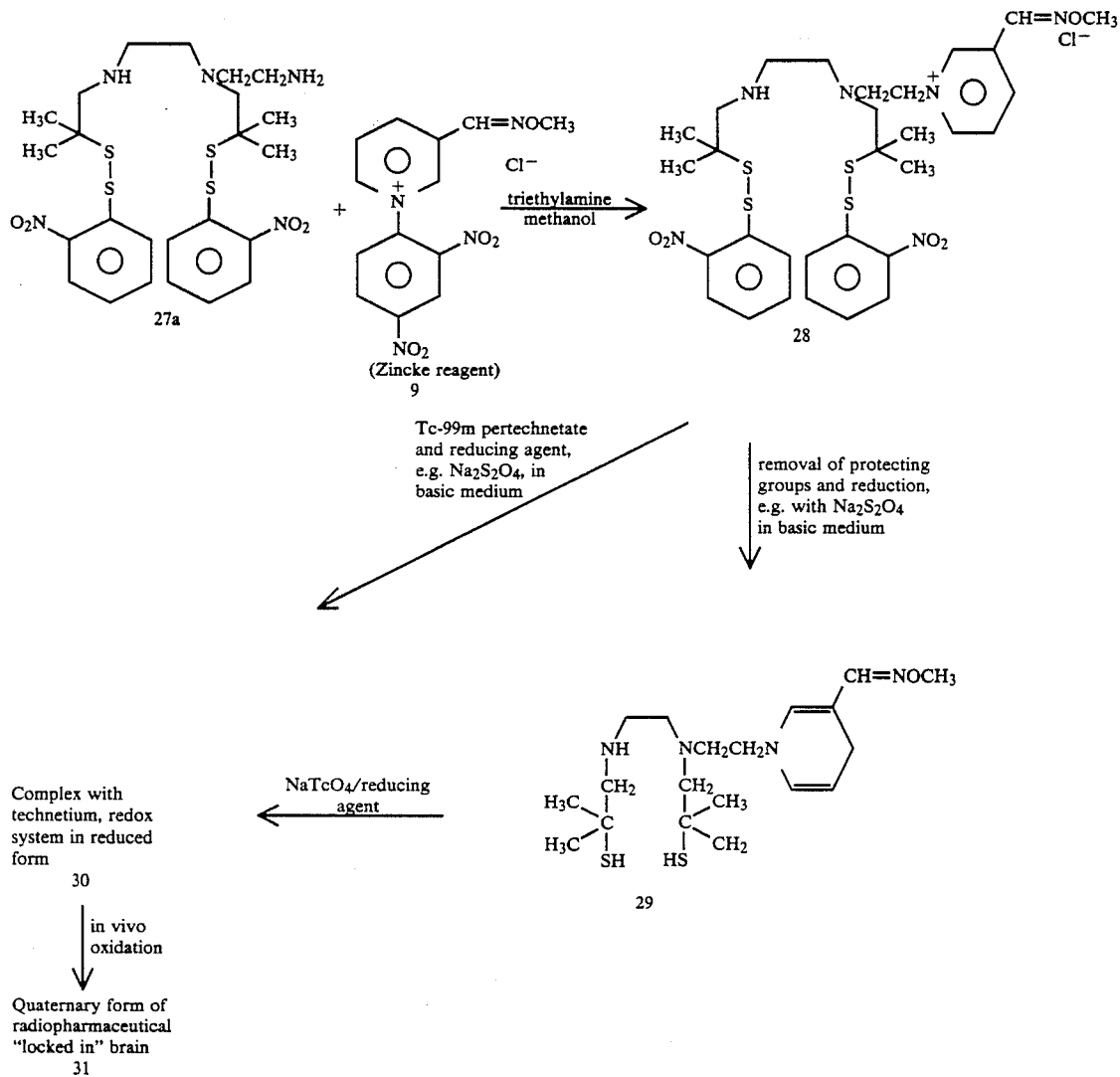
SCHEME 4
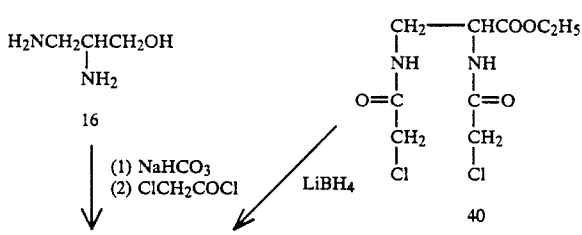

4,963,682
SCHEME 4
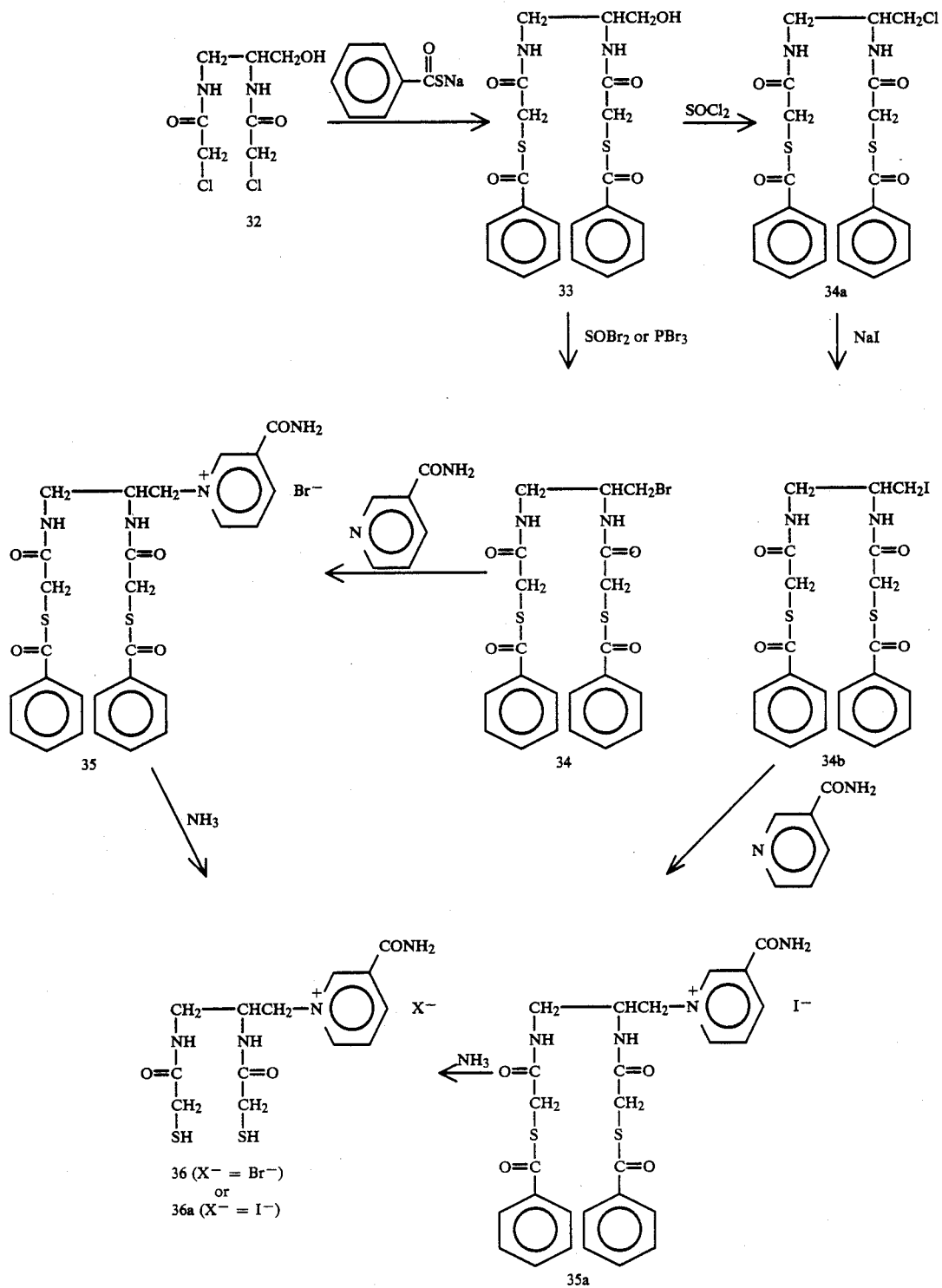

-continued
SCHEME 4
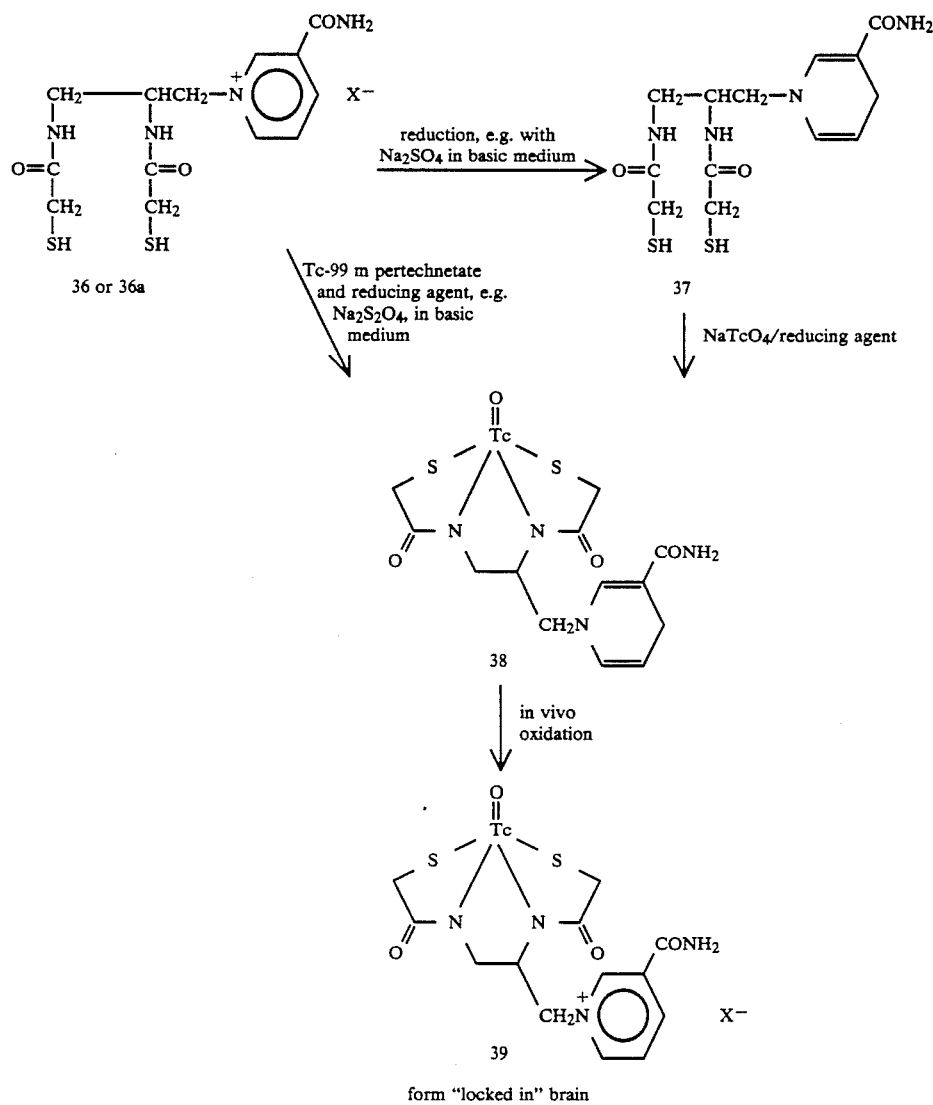
SCHEME 5
PART A:
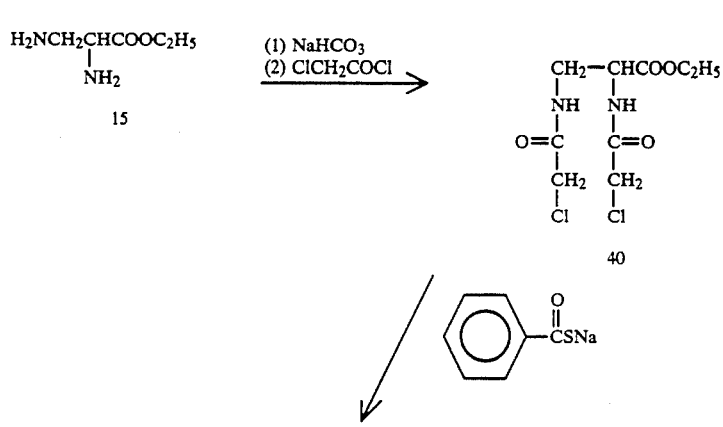

-continued
SCHEME 5
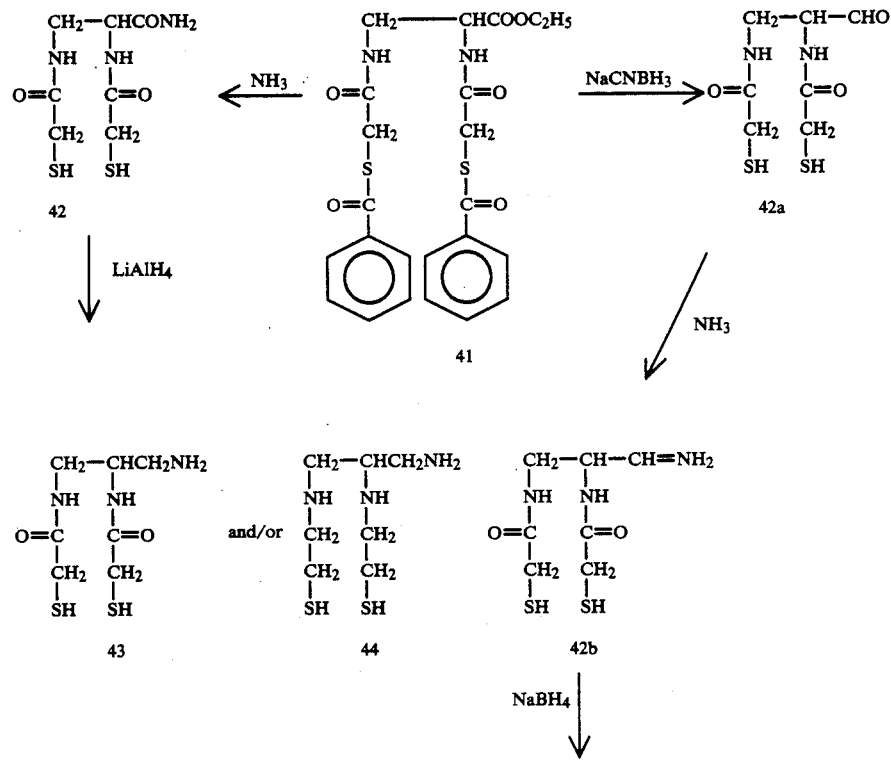
PART B, version 1:
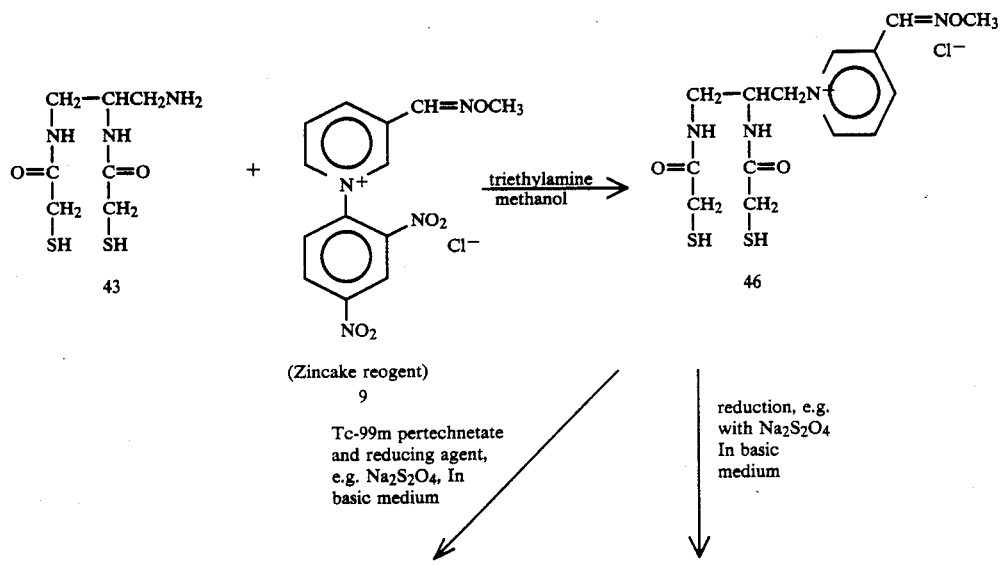

-continued
SCHEME 5
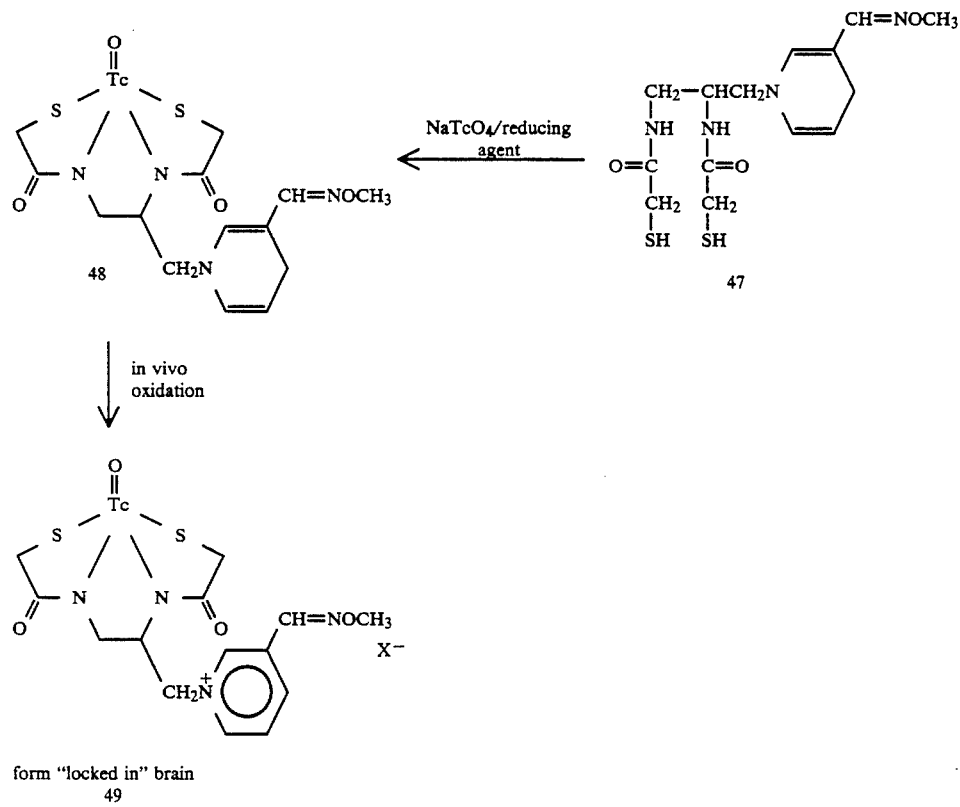
form "locked in" brain
49
SCHEME 6
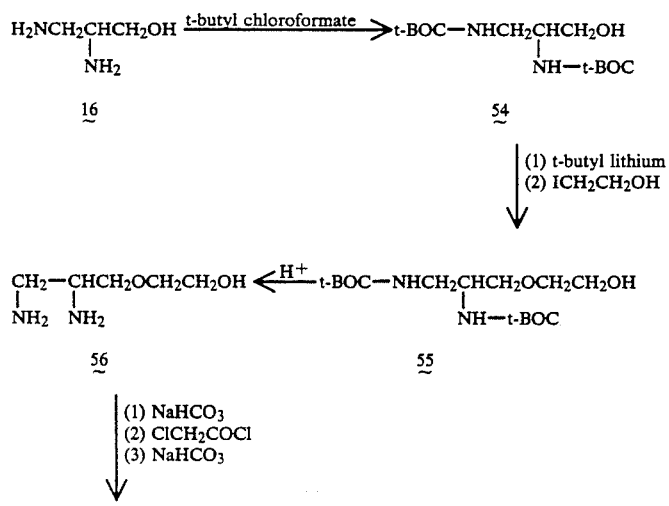

SCHEME 6
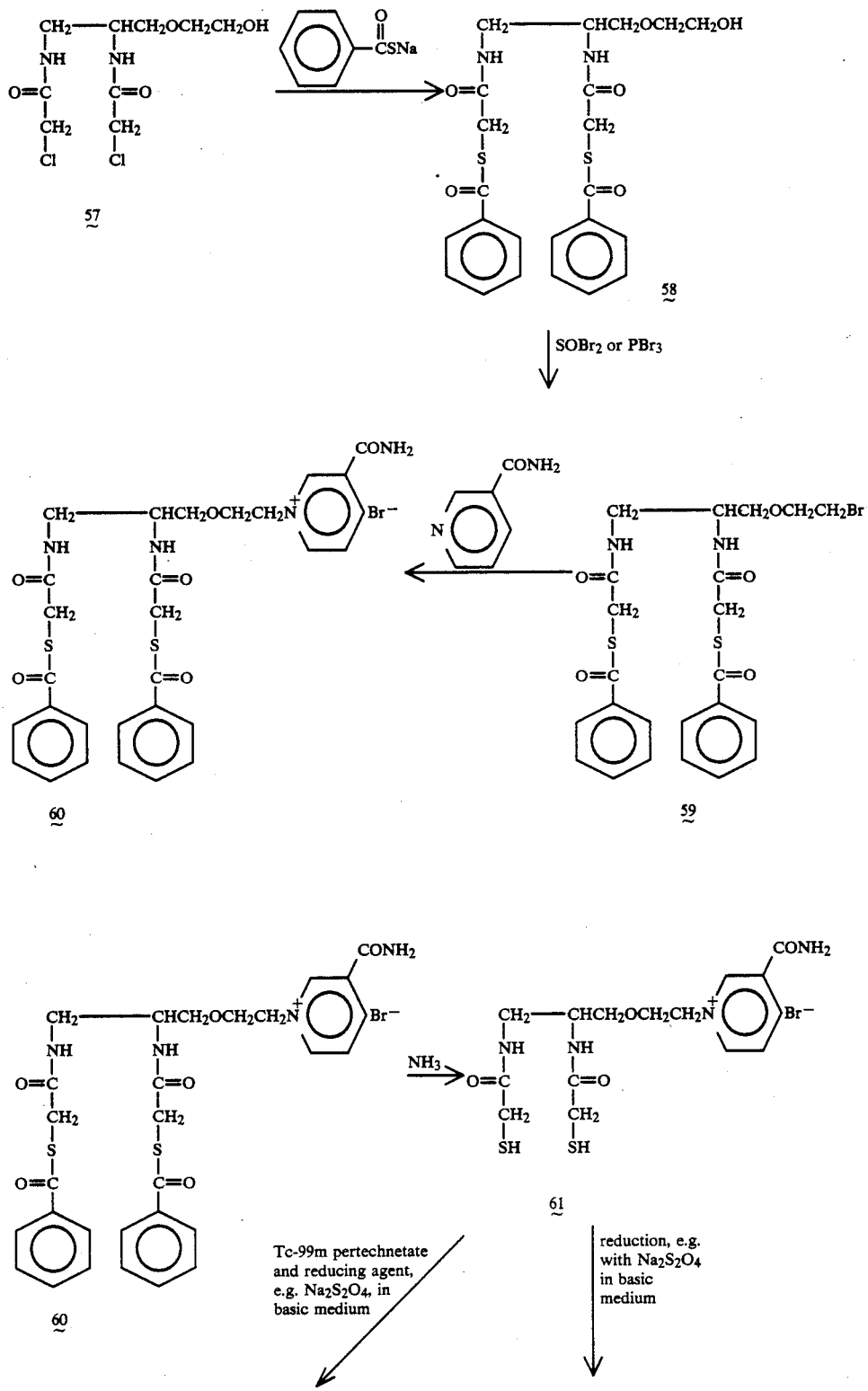

-continued
SCHEME 6
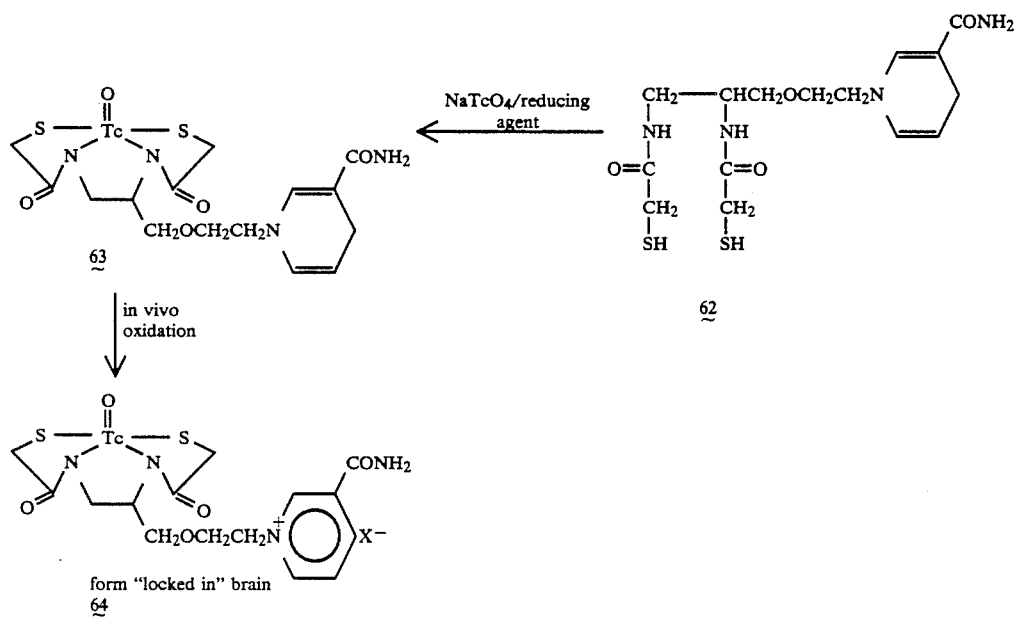
SCHEME 7
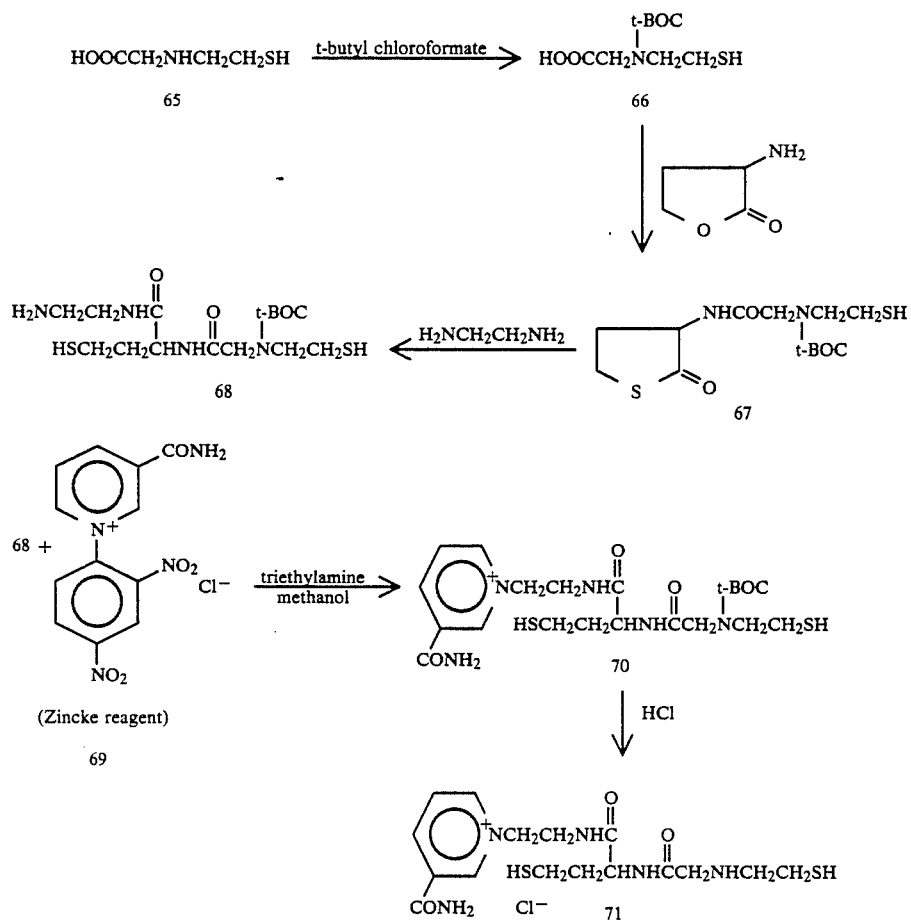

-continued
SCHEME 7
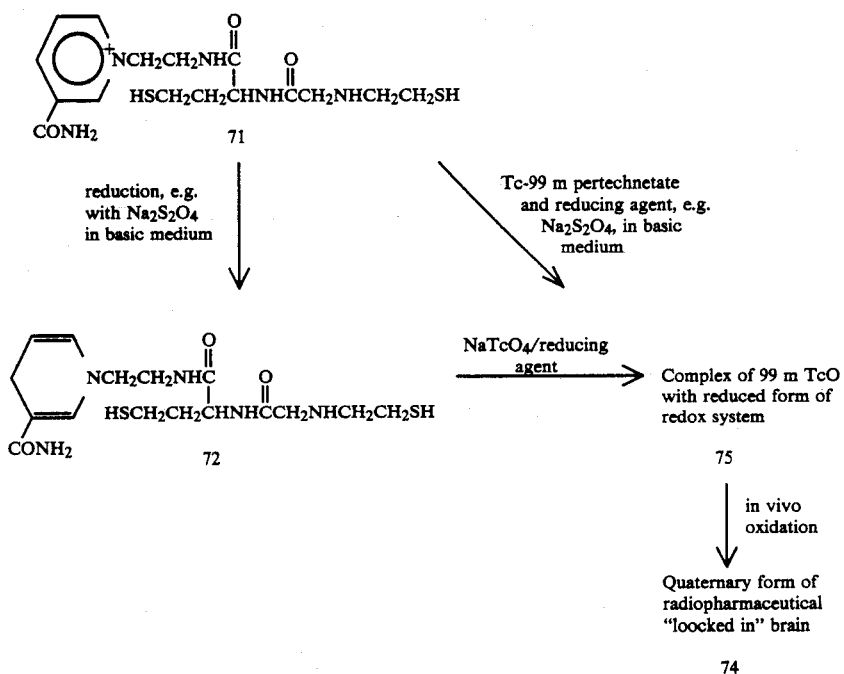
SCHEME 8
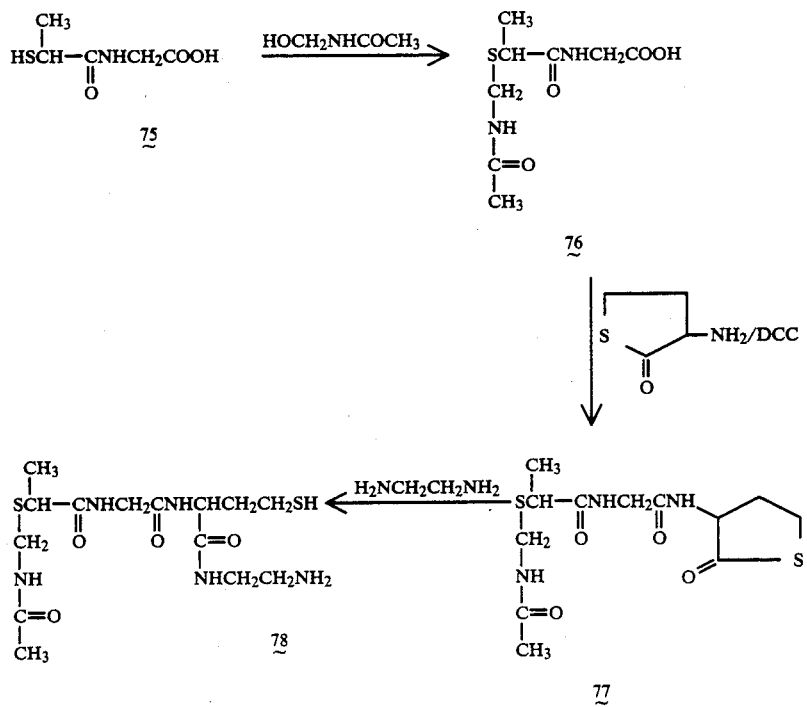

-continued
SCHEME 8
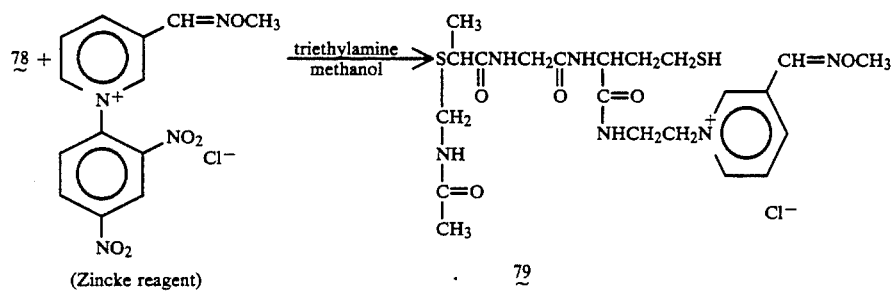
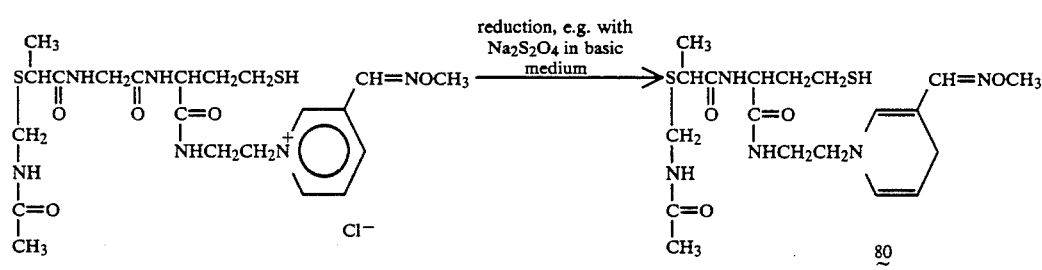
Tc-99m pertechnetate and reducing agent, e.g. Na2S2O4, in basic medium
NaTcO4/reducing agent
Complex with technetium, redox system in reduced form
81
in vivo oxidation
Quaternary form of radiopharmaceutical "locked in" brain
82
SCHEME 9
PART A:
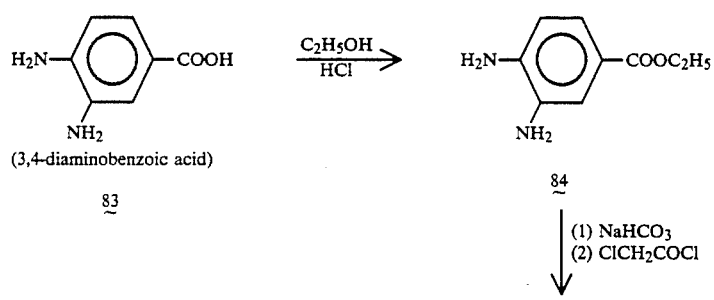
(1) NaHCO3
(2) ClCH2COCl -continued
SCHEME 9
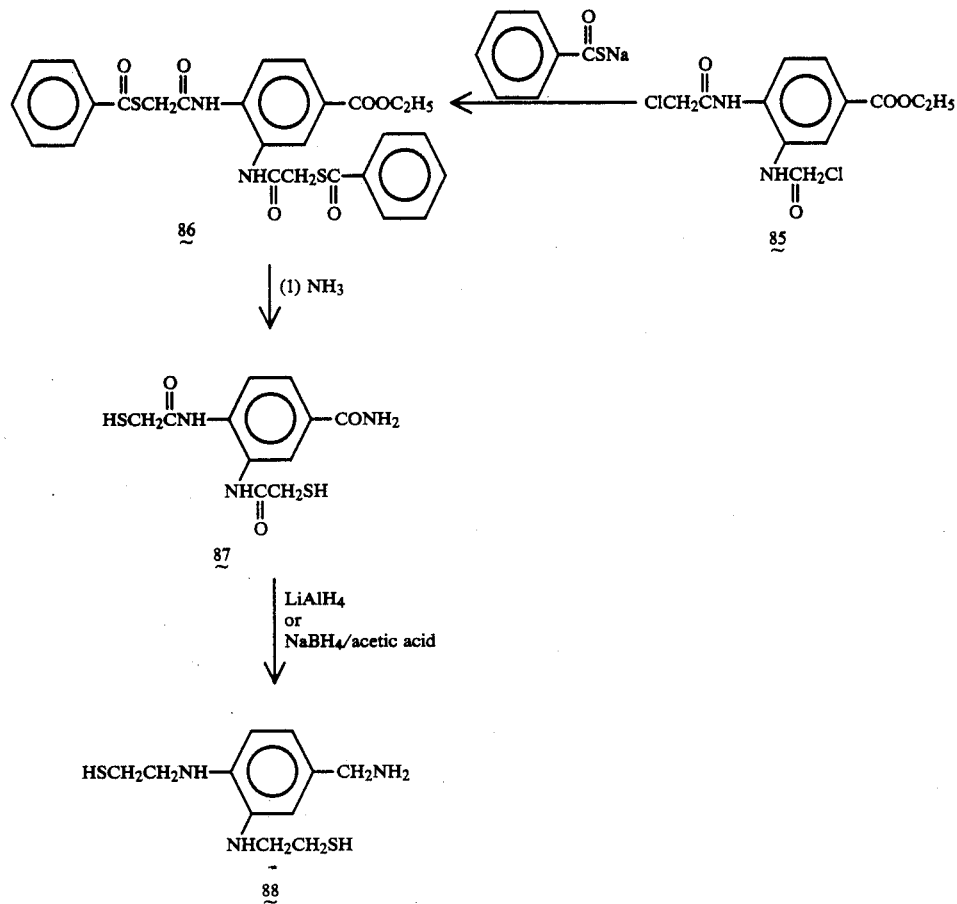
PART B, version 1:
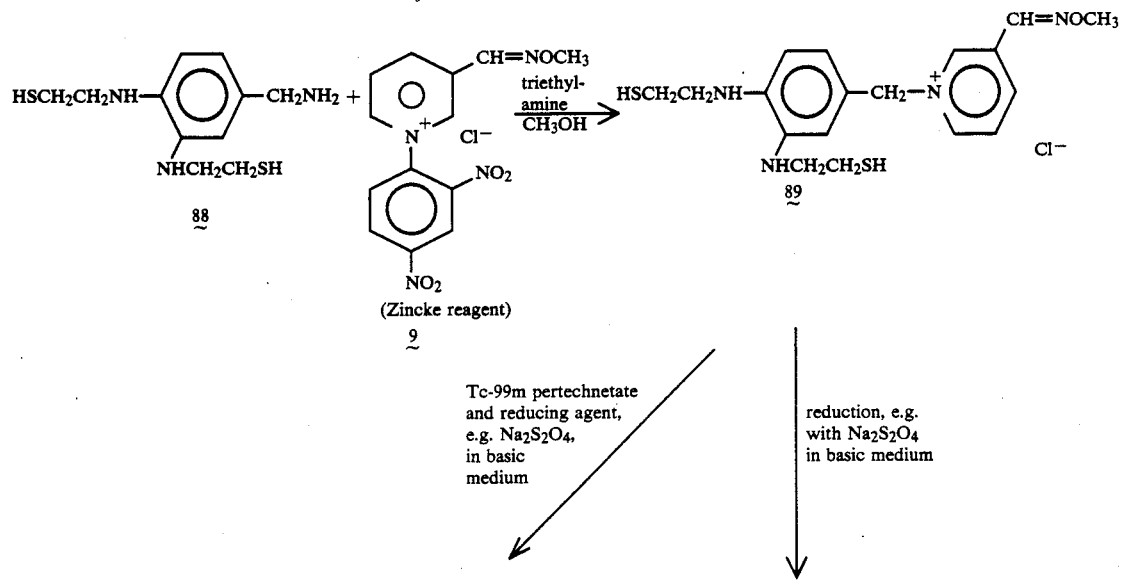

SCHEME 9
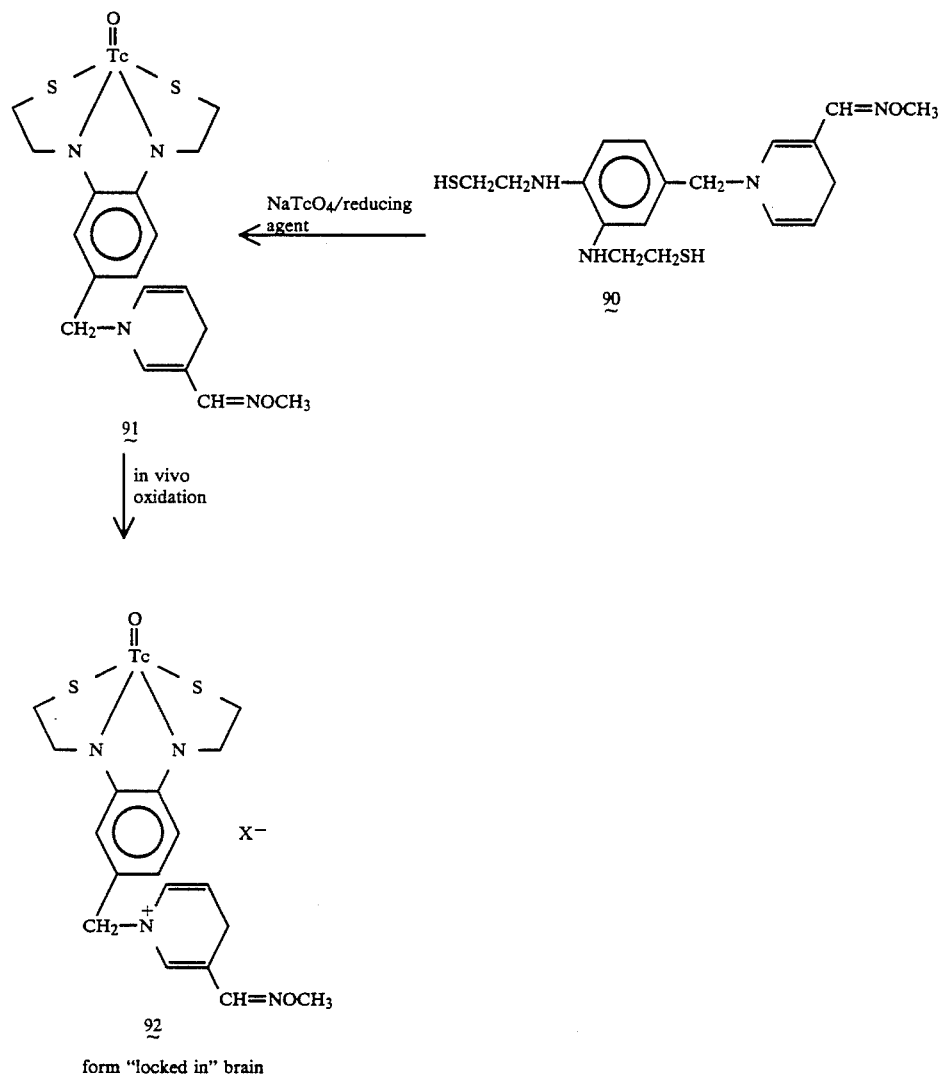
PART B, version 2:
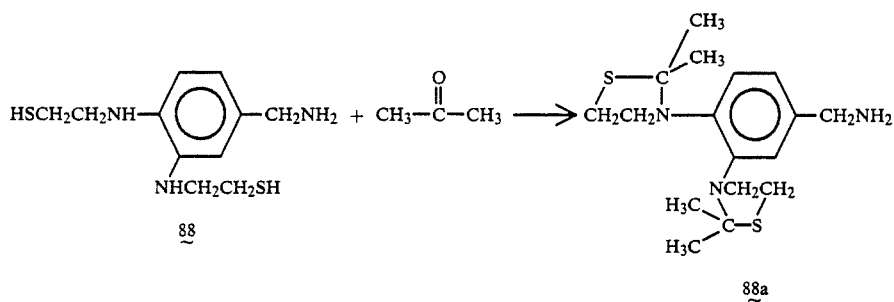

-continued
SCHEME 9
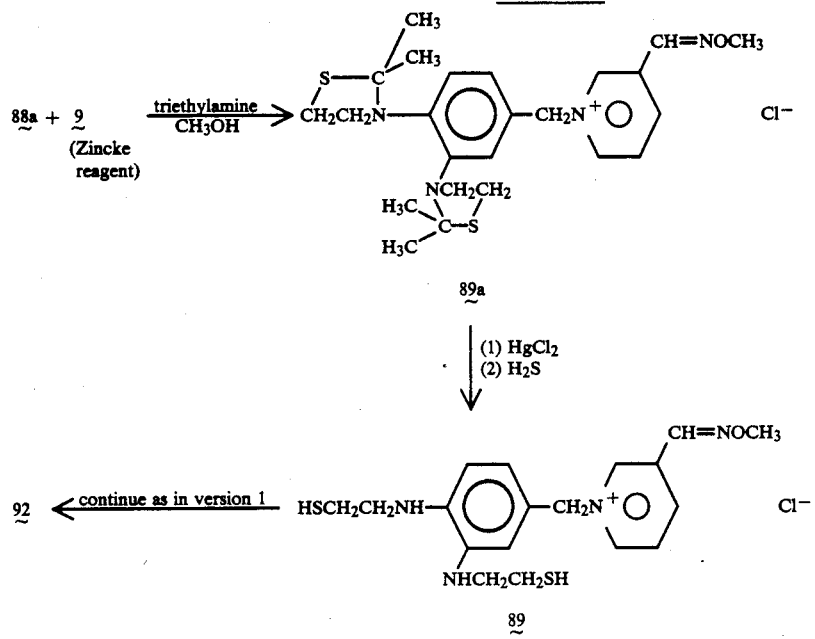
SCHEME 10
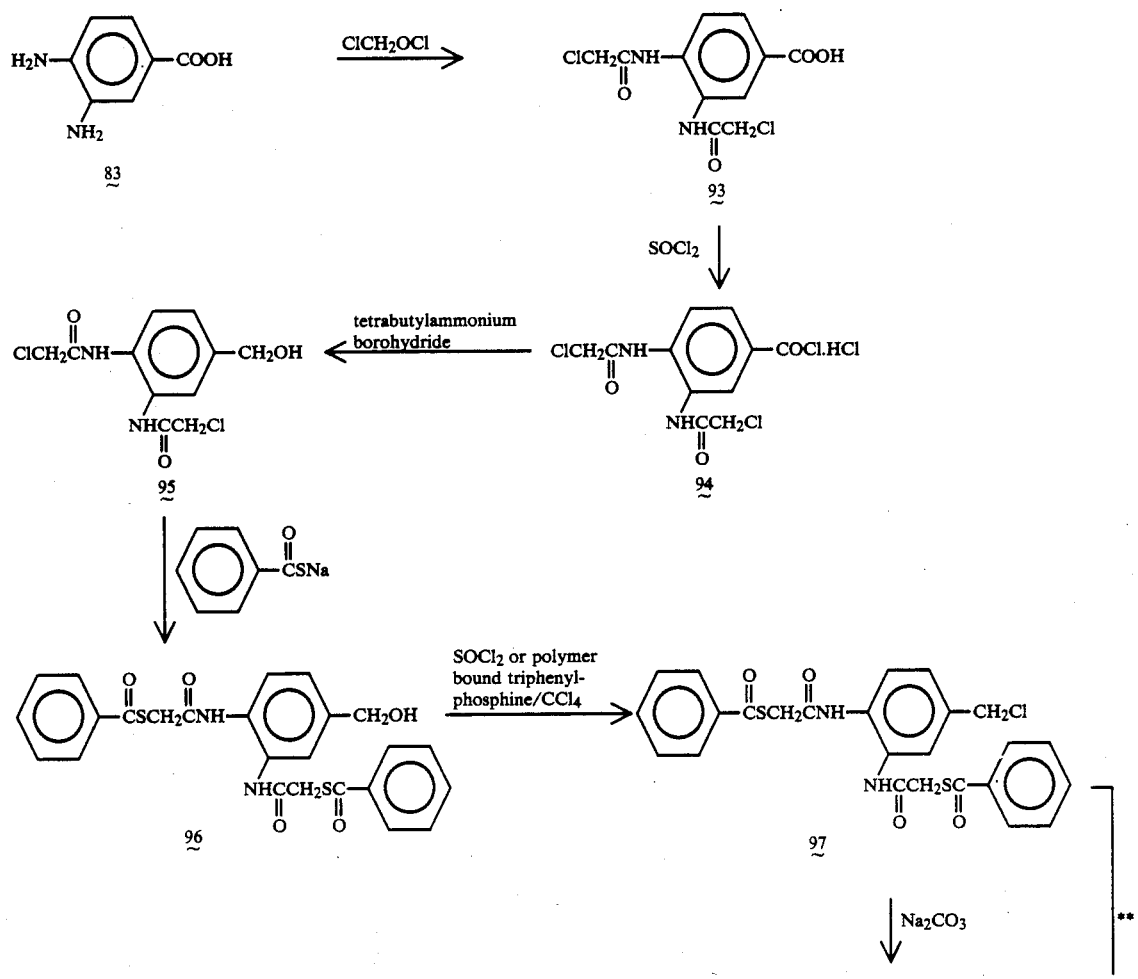

-continued
SCHEME 10
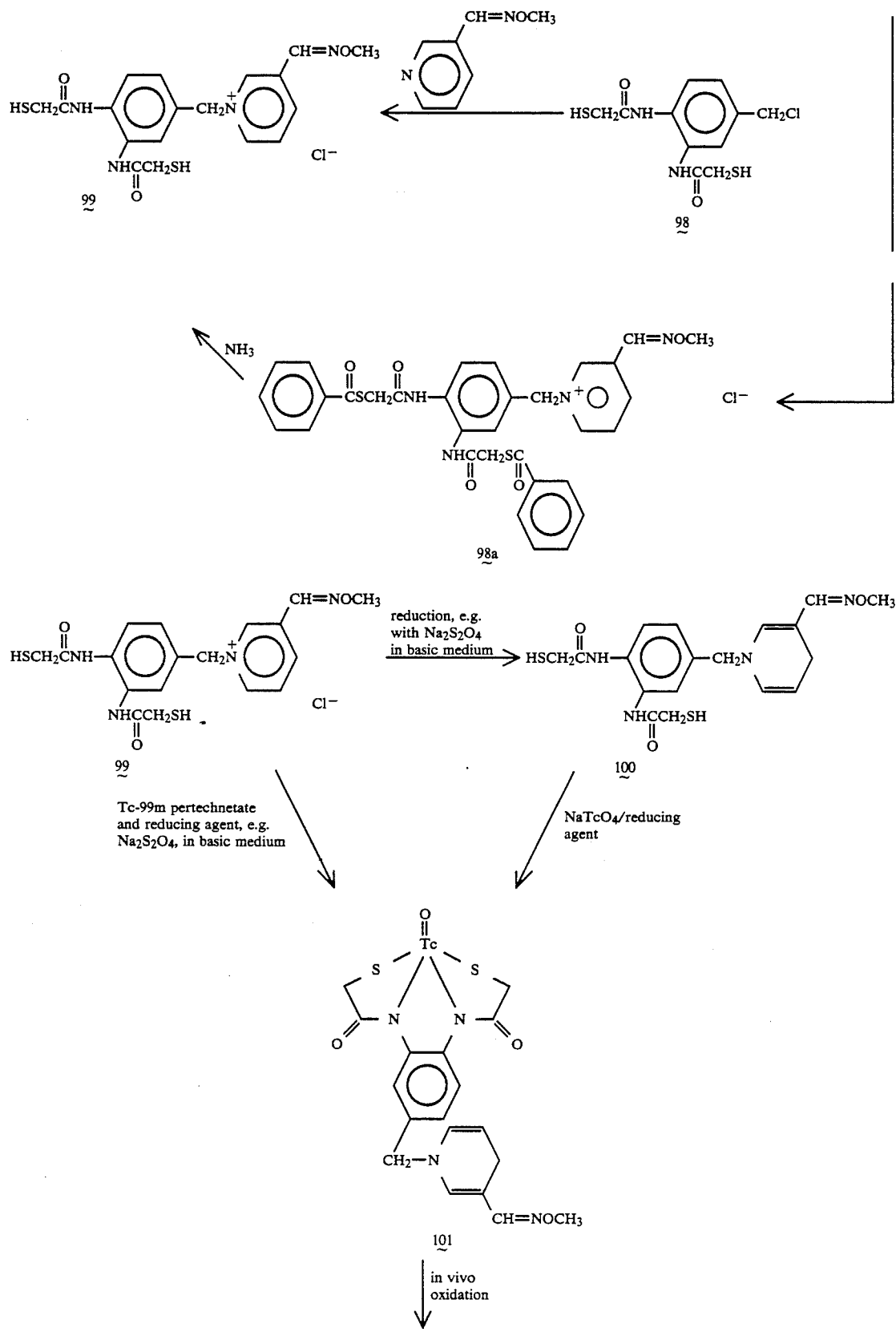

-continued
SCHEME 10
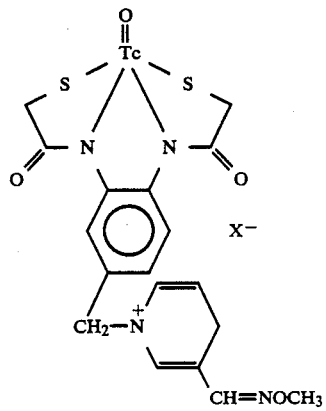
form "locked in" brain
Note:
** N 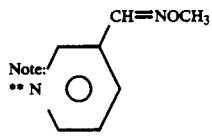
SCHEME 11
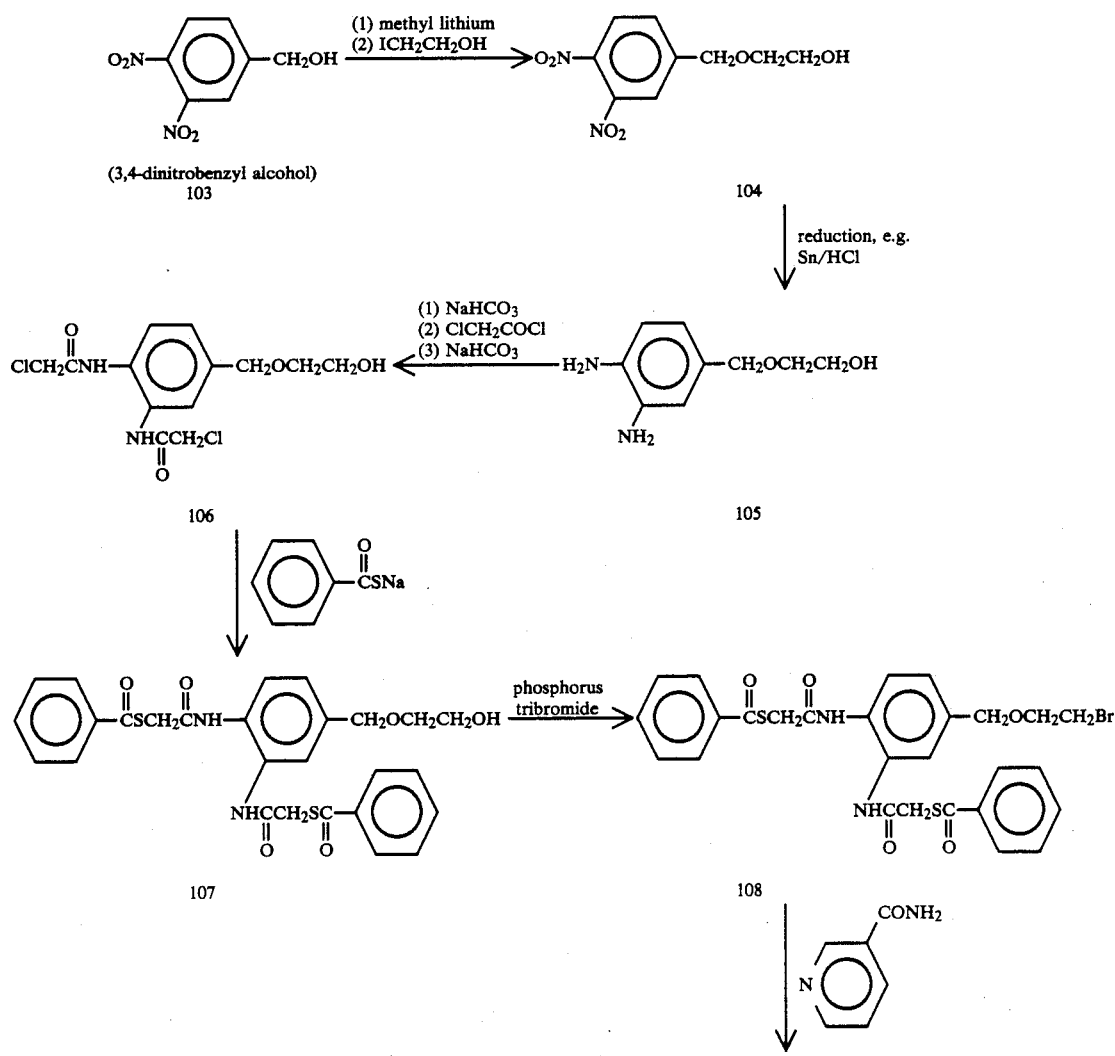

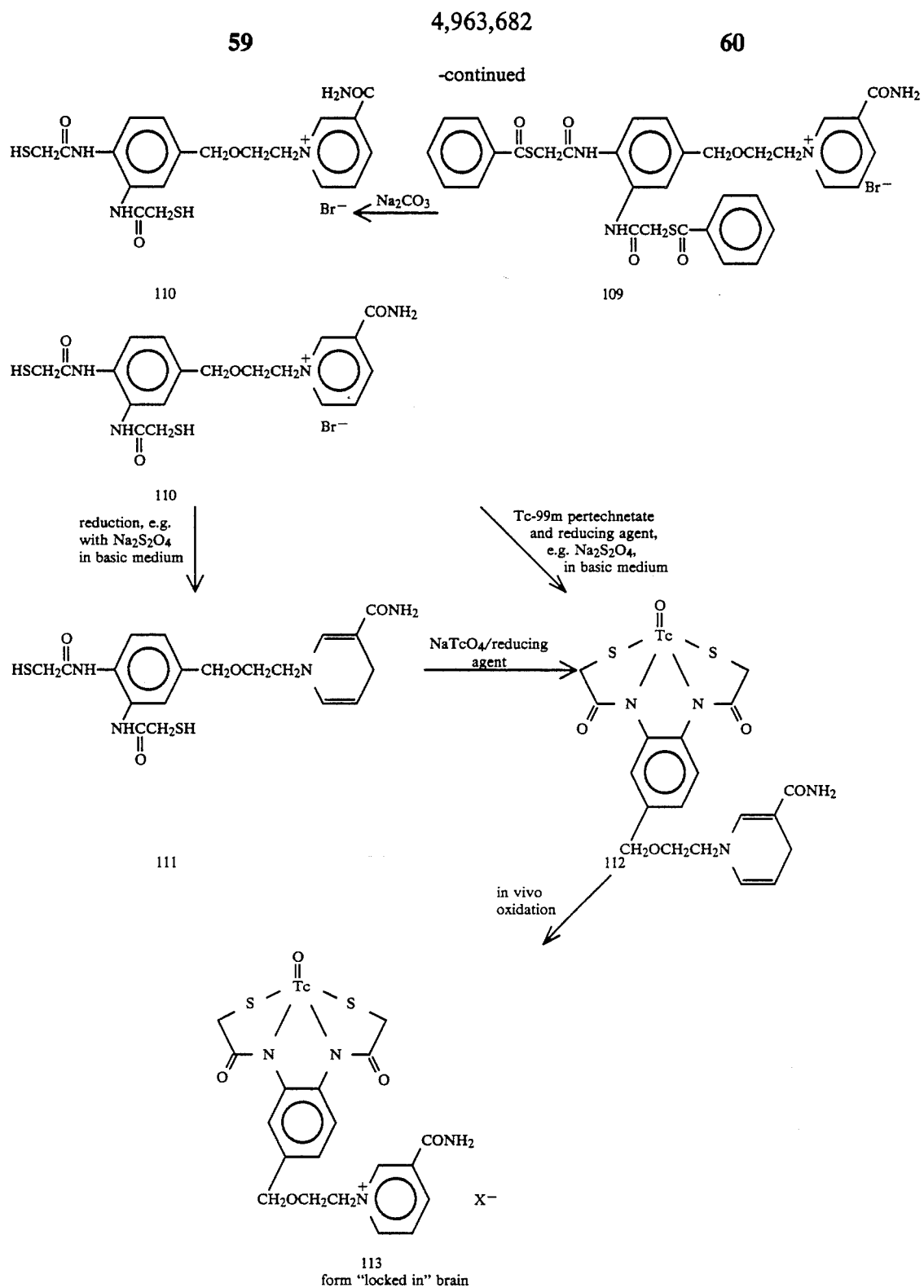

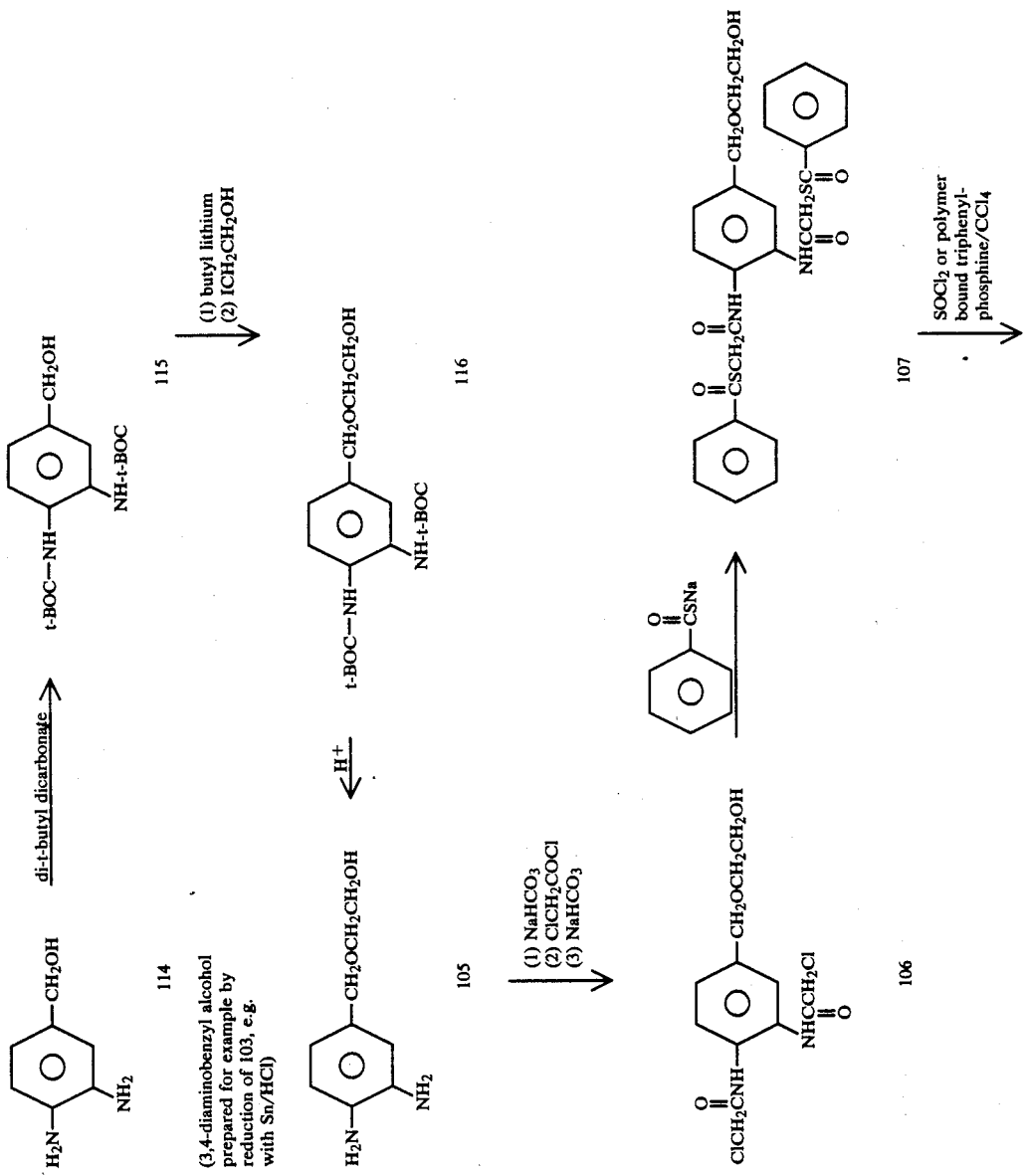

-continued
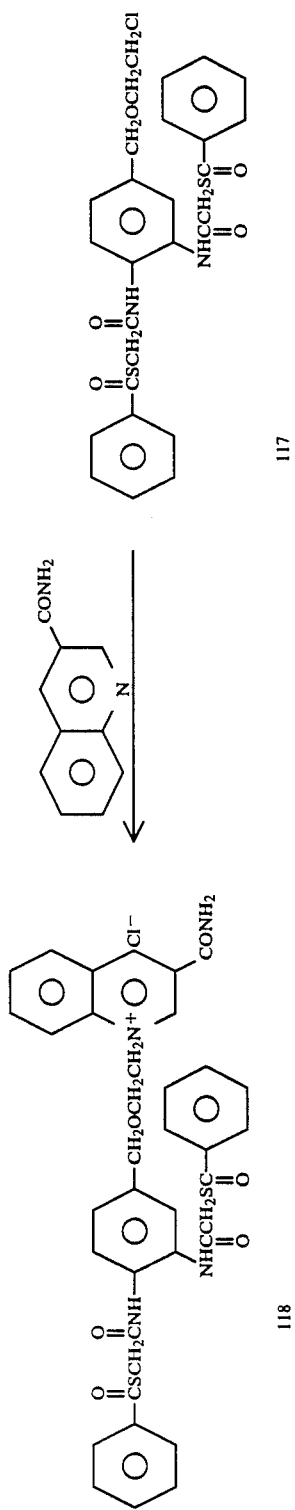
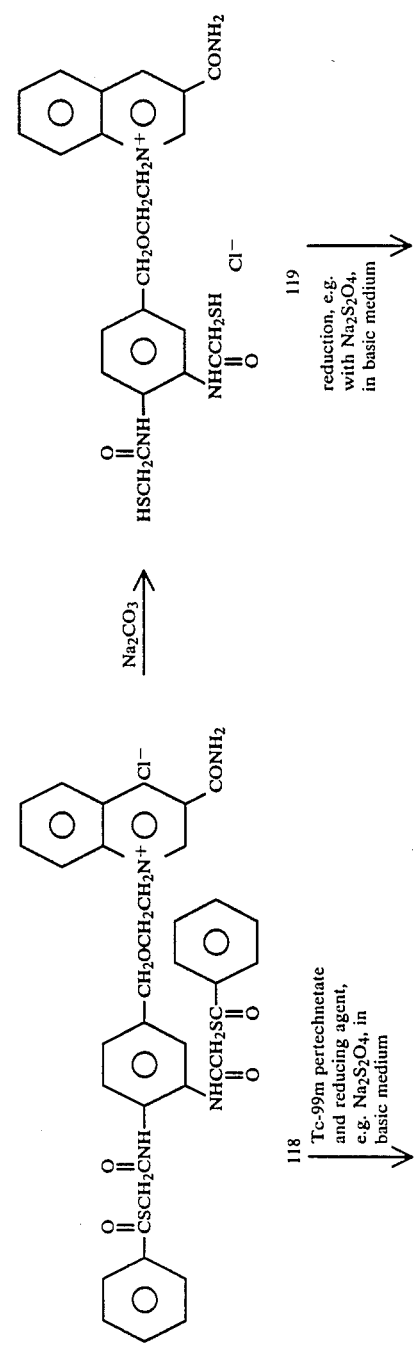

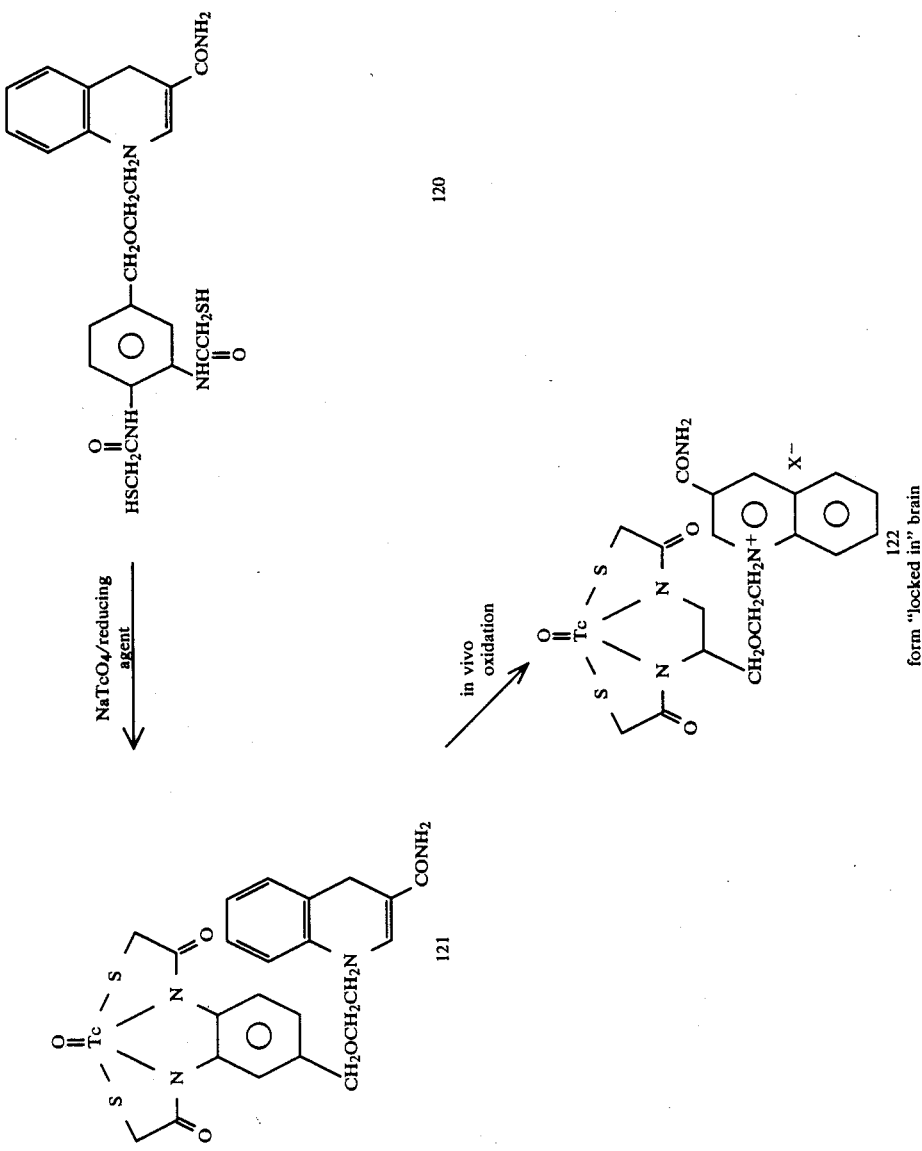

SCHEME 13

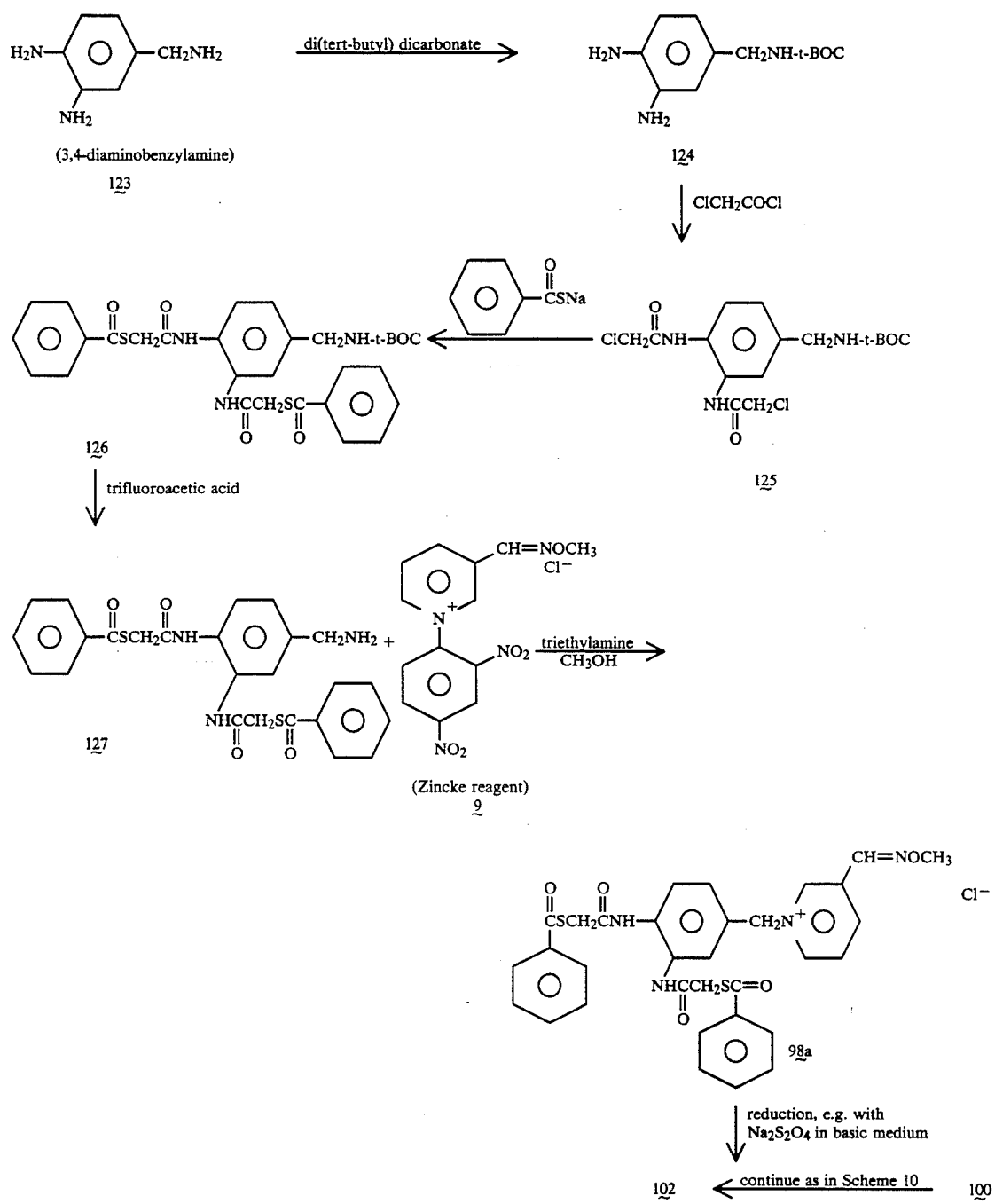

Thus, Schemes 1 (version 1), 5 (versions 1 and 2) and 9 (version 1) above illustrate typical conversion of a carboxylic acid ester group to the corresponding amide (—CONH$_2$); reduction of the amide function to the corresponding amine (—CH$_2$NH$_2$); replacement group with the desired quaternary function

, utilizing a Zincke reagent; and reduction resultant quaternary of formula (I) to the corresponding dihydro of formula (II), or conversion of (I) directly to the formula (III) radiopharmaceutical. Variations of this type of reaction sequence are shown in versions 2 and 3 of Scheme 1, version 3 of Scheme 5 and version 2 of Scheme 9, in which a protecting group is introduced prior to reaction with the Zincke reagent and then removed prior to reduction of the quaternary function. In the case of the chelating agents shown in these schemes, reaction with acetone protects both the secondary amino and thiol functions by formation of thiazolidine structures so that those functions do not interfere in the reaction with the Zincke reagent. Subsequently, the secondary amino and mercapto groups are regenerated by reacting the protected intermediate with mercuric chloride in an organic solvent such as methanol, conveniently at room temperature, and then decomposing the resulting complex with hydrogen sulfide. See, for example British Patent Specification No. 585,250, which utilizes such a procedure for the production of esters of penicillamine.

Schemes 2 (version 1), 4 and 10 above illustrate typical conversion of an alcohol (—CH₂OH). which may be obtained from the corresponding carboxylic acid ester, to the corresponding halide (—CH₂Cl or —CH₂Br); reaction of the halo derivative with the appropriate pyridine derivative

to afford the desired formula (I) quaternary; and reduction to the corresponding formula (II) dihydro or conversion directly to the corresponding formula (III) radiopharmaceutical. Schemes 4 and 10 also illustrate removal of a protecting group immediately after formation of the quaternary while version 2 of Scheme 2 illustrates introduction and removal of the thiazolidine protecting group discussed above with respect to versions 2 and 3 of Scheme 1, etc.

In Scheme 3 above, there is shown a typical method for introducing a longer alkylene chain between an atom which is involved in forming the chelate structure and a pendant NH₂ group which is to be replaced with the quaternary structure. As depicted in this scheme a secondary amino group >NH is reacted with a haloalkamide, e.g. BrCH₂CONH₂, replacing the hydrogen of the >NH with —CH₂CONH₂. Reduction of the amide affords the corresponding >NCH₂CH₂NH₂ compound. That amine can then be reacted with a Zincke reagent to replace the —NH₂ with

followed by reduction as in the other schemes; preferably, however, any free thiol groups are protected prior to reaction with the Zincke reagent.

Schemes 6, 11 and 12 illustrate yet other methods for lengthening the alkylene chain, the chain here being interrupted by one or more oxygen atoms. Thus, a —CH₂OH group is typically converted to the corresponding lithium salt and then reacted with an iodoalkanol, e.g. ICH₂CH₂OH, to convert the —CH₂O—Li⁺ group to a —CH₂OCH₂CH₂OH group. [Obviously, the chain could be lengthened by utilizing a longer-chain iodoalkanol, or by repeating the two steps just described (in which case additional intervening oxygen atoms would be introduced.)] The —CH₂OCH₂CH₂OH group is then converted to the corresponding —CH₂OCH₂CH₂Br or —CH₂OCH₂CH₂Cl, which is then reacted with the selected pyridine derivative

to form the desired quaternary salt. In the schemes shown, a protecting group is removed immediately after quaternization to afford the formula (I) quaternary, which is subsequently reduced as in the other schemes.

In Schemes 7, 8 and 13 above, replacement of an —NH₂ group with the corresponding quaternary

is shown, utilizing a Zincke reagent. Where appropriate, quaternary formation is followed by removal of protecting groups, as in Schemes 7 and 13. The resultant formula (1) quaternary is then reduced as shown in the other schemes.

Many of the earliest steps in the reaction schemes depicted above parallel reactions described in Fritzberg U.S. Pat. No. 4,444,690. See, for example, the conversion of 14 to 15 in Scheme 2; the conversion of 16 to 32 to 33 in Scheme 4; the conversion of 15 to 40 to 41 in Scheme 5; the conversion of 56 to 57 to 58 and the conversion of 60 to 61 in Scheme 6; and so on.

Similar schemes can be shown for the preparation of the other derivatives of this invention. The steps of introducing and removing protecting groups are only included when necessary. Also, the order of steps may be altered; in particular, quaternization may occur earlier in the reaction scheme, depending of course on the particular compounds involved. Other reaction schemes, reactants, solvents, reaction conditions, etc. will be readily apparent to those skilled in the art. Also, insofar as concerns the quaternary derivatives, when an anion different from that obtained is desired, the anion in the quaternary salt may be subjected to anion exchange via an anion exchange resin or, more conveniently, by use of the method of Kaminski et al, *Tetrahedron*, Vol. 34, pp. 2857-2859 (1978). According to the Kaminski et al method, a methanolic solution of an HX acid will react with a quaternary ammonium halide to produce the methyl halide and the corresponding quaternary X salt.

The processes exemplified by Schemes 1, 3, 5, 7, 8, 9 and 13 include the step of reacting a compound containing an —NH₂ group with a Zincke reagent. The Zincke reaction can be to derive the instant derivatives in which

is the residue of a primary amine, or their protected counterparts, directly from the corresponding primary amine/parent chelating agent. However, if it is des prepare the instant derivatives in which

is the residue of a secondary or tertiary amine, or protected counterparts, via the Zincke reaction, then one will not use the parent secondary or tertiary amine chelating agent as the starting material but would instead use the corresponding primary amine as the starting material. Alternatively, a compound of the formula

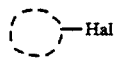

wherein Hal is chloro or bromo and

is the residue of the chelating agent as defined or its protected counterpart can be reacted with a pyridine derivative of the formula

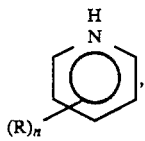

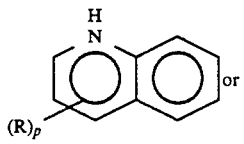

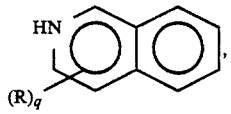

wherein R, n, p and q are defined with formula (I), e.g. nicotinamide, isonicotinamide, picolinamide, 3-quinolinecarboxamide, 4-isoquinolinecarboxamide or the corresponding oximes in which a —CH=NOCH₃ group is present in place of the —CONH₂ group of nicotinamide etc. See, for example, Schemes 2, 4, 6, 10, 11 and 12. The starting pyridine derivatives are readily available or can be prepared in known manner, e.g. 3-quinolinecarboxamide can be prepared by treating the corresponding acid with ammonia.

When a Zincke reagent is utilized in the reaction sequence, such reagent can be prepared by reacting 1-chloro-2,4-dinitrobenzene with a compound of the formula

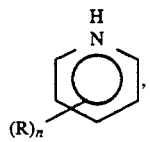

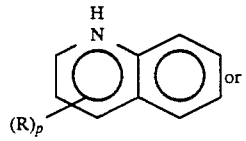

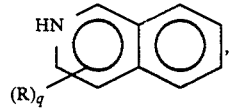

wherein R, n, p and q are defined as with formula (I), to afford the corresponding Zincke reagent of the formula

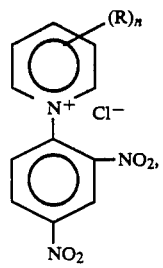

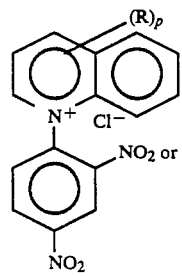

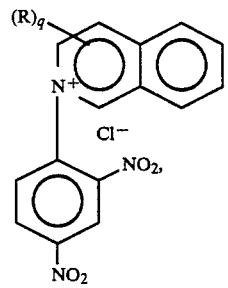

respectively. Thus, for example, the specific Zincke reagent depicted in Scheme 7 can be prepared by reacting nicotinamide with 1-chloro-2,4-dinitrobenzene. See also Zincke et al, *Annalen*, 1904, 333, 296; Lettre et al, *Annalen*, 1953, 579, 123; Keijzer et al, *Heterocycles*, Vol. 16, No. 10, 1981, 1687. Preferred Zincke reagents are those in which n, p or q is one and R is —CONH₂ or —CH=NOCH₃ and is located in the 3-position of the pyridinium or quinolinium structure or in the 4-position of the isoquinolinium structure. Typically, the Zincke reagent is reacted with the primary amine, which may be very conveniently employed in the form of its acid addition salt, in the presence of a suitable base, e.g. triethylamine, in an appropriate organic solvent, e.g. methanol, to afford the desired quaternary salt.

When a starting material of the formula

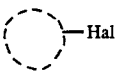

wherein

and Hal are defined above is utilized to prepare the quaternary salt, said starting material can be prepared from the corresponding alcohol, e.g. by methods such as those depicted in Schemes 2, 4, 6, 10, 11 or 12.

Reduction of the quaternary salt of formula (I) to the corresponding dihydro derivative of formula (II) can be conducted at a temperature from about −10° C. to room temperature, for a period of time from about 10 minutes to 2 hours, conveniently at atmospheric pressure. Typically, a large excess of reducing agent is employed. e.g., a 1.5 molar ratio of reducing agent to starting compound of formula (I). The process is conducted in the presence of a suitable reducing agent, preferably an alkali metal dithionite such as sodium dithionite or an alkali metal borohydride such as sodium borohydride or lithium aluminum borohydride, in a suitable solvent. Sodium dithionite reduction is conveniently carried out in an aqueous solution; the dihydro product of formula (II) is usually insoluble in water and thus can be readily separated from the reaction medium. In the case of sodium borohydride reduction, an organic reaction medium is employed, e.g., a lower alkanol such as methanol, an aqueous alkanol or other protic solvent. More typically, however, the quaternary of formula (I) is reduced in the same reaction mixture as the reduction of the radionuclide (preferably technetium) to an appropriate oxidation state, affording the formula (III) radiopharmaceutical in one step from the formula (I) quaternary. Further details of the one-step reduction are given hereinbelow.

It will be apparent from the foregoing that a wide variety of derivatives of formulas (I) through (IV) can be obtained in accord with this invention. In a particularly preferred embodiment of this invention, however, there are provided novel chelating agent precursors of the formula

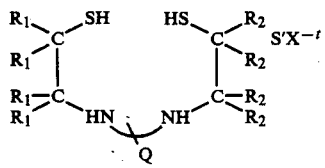

wherein each $R_1$ is independently selected from the group consisting of H and $C_1$-$C_7$ alkyl, or an $R_1$ can be combined with the adjacent >C—$R_1$ such that

represents >C=O; each $R_2$ is independently selected from the group consisting of H and $C_1$-$C_7$ alkyl, or an $R_2$ can be combined with the adjacent >C—$R_2$ such that

represents >C=O;

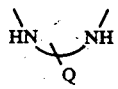

is a radical of the formula

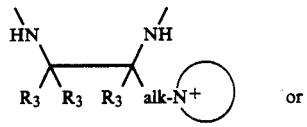

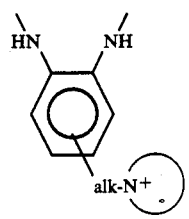

wherein each $R_3$ is independently selected from the group consisting of H and $C_1$-$C_7$ alkyl, alk is a straight or branched lower alkylene group ) which additionally may contain 1, 2 or 3 nonadjacent oxygen atoms in the chain, and

is as defined with formula (I) hereinabove; $X^-$ and t are as defined with formula (I); and s' is a number which when multiplied by t is equal to one. Preferably, the salts of formula (Ia) have the partial structure

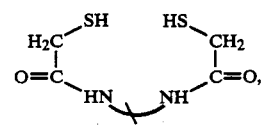

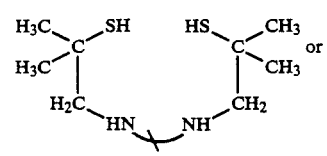

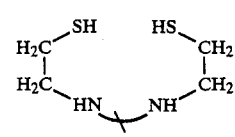

or are position isomers and/or homologs of the first two partial structures shown. It is also preferred that when

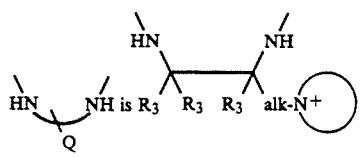

then each $R_3$ is preferably H and alk is preferably a $C_1$-$C_6$ alkylene group, or a $C_1$-$C_6$ alkylene group interrupted by an oxygen atom in the chain; and that when

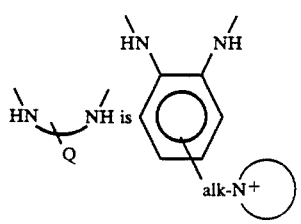

then alk is preferably a $C_1$-$C_6$ alkylene group, or a $C_1$-$C_6$ alkylene group interrupted by an oxygen atom in the chain. Preferred values for

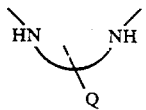

in formula (Ia) are as given in conjunction with formula (I) hereinabove.

Corresponding to the preferred novel chelating agent precursors of formula (Ia) are the preferred novel chelating agents of the formula

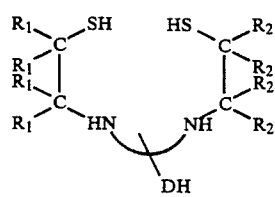 (IIa)

wherein $R_1$ and $R_2$ are as defined with formula (Ia) and

is a radical of the formula

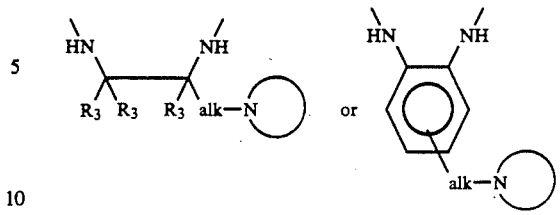

wherein $R_3$ and alk are as defined with formula (Ia) and

is as defined with formula (II) hereinabove. Preferred compounds of formula (IIa) are the dihydro derivatives corresponding to the preferred compounds of formula (IIa).

Likewise preferred are the novel radiopharmaceuticals in which a formula (IIa) compound is chelated with a radioactive metal, especially with technetium. Especially preferred radiopharmaceuticals have the formula

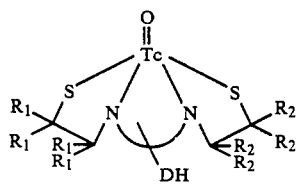 (IIIa)

wherein $R_1$ and $R_2$ are as defined with formula (Ia) and

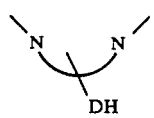

is a radical of the formula

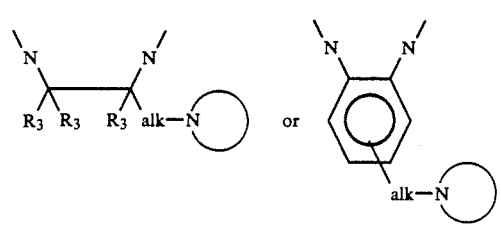

wherein $R_3$ and alk are as defined with formula (Ia) and

is as defined with formula (II) hereinabove; and the corresponding quaternaries, especially those of technetium, "locked in" the brain, which have the formula

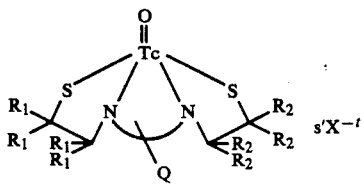 (IVa)

wherein $R_1$, $R_2$, $s'$, $X^-$ and t are as defined with formula (Ia) and

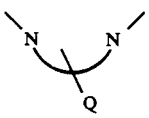

is a radical of the formula

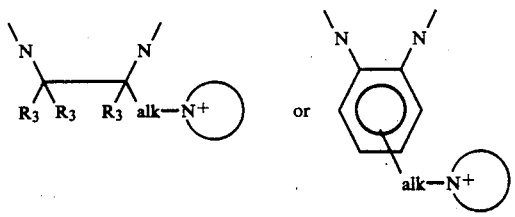

wherein $R_3$ and alk are as defined with formula (Ia) and

is as defined with formula (I) hereinabove. The preferred complexes of formulas (IIIa) and (IVa) are those which correspond to the preferred derivatives of formulas (Ia) and (IIa).

In order to further illustrate the present invention and the advantages thereof, the following specific examples are given, it being understood that same are intended only as illustrative and in no wise limitative.

EXAMPLE 1

To a stirred solution containing 115.6 g (1.6 mol) of isobutyraldehyde 1 in 184 g of carbon tetrachloride are added dropwise, at 40°–50° C., 108 g (0.8 mol) of 97% sulfur monochloride. The addition is carried out during a 2.5 hour period, under a nitrogen atmosphere, with occasional cooling. The solution is maintained at 30°–45° C., with stirring, for an additional 48 hour period, under a current of nitrogen, to remove the hydrogen chloride liberated. The solution is distilled under vacuum to give 72 g of the desired 3,4-dithia-2,2,5,5-tetramethylhexane-1,6-dione, i.e. Compound 2 of Scheme 1. $^1$H NMR(CDCl$_3$) δ 9.1(s,2—CHO), 1.4[s,12,—C(CH$_3$)$_2$—].

EXAMPLE 2

To 10 g (0.07 mol) of ethyl cyanoglyoxylate-2-oxime 3 are added 125 mL of absolute ethanol, 15 g of hydrogen chloride gas and 1 g of platinum oxide. The mixture is hydrogenated using a Parr-hydrogenation apparatus. Hydrogen uptake is complete in 3 hours. The product is removed by filtration and taken up in 75 mL of hot 95% ethanol. The ethanol solution is filtered. The filtrate is then cooled and the crystalline product which separates on standing is removed by filtration. There is thus obtained ethyl 2,3-(diammonium)propionate dichloride, i.e. Compound 4 of Scheme 1. Yield 5 g (35%). melting point 164°–166° C. (lit. 164.5°–65° C.): $^1$H NMR(D$_2$O) δ 4.5(m.3.—NCHCO—, —OCH$_2$CH$_3$), 3.5(m,2,—NCH$_2$-CH—), 1.3(t,3,—OCH$_2$CH$_3$).

EXAMPLE 3

Procedure I

To 1.0 g (5 mmol) of the bisaldehyde 2 is added dropwise a solution of 1.0 g 15 mmol) of the ester 4 and 0.9 mL of pyridine in 30 mL of methanol at 0° C. while under a nitrogen atmosphere. The addition takes place during a 10 minute period. The solution is then allowed to stand for 1 hour, after which time 10 mL of water is added. The solution turns turbid and warms to 26° C. The solution is stirred for an additional 20 minute period, after which time the white precipitate which forms settles out of solution. The precipitate is removed by filtration and then is taken up in chloroform. The chloroform solution is dried over sodium sulfate. Removal of the solvent and trituration of the residue with petroleum ether gives white plate-like crystals of the desired product, 5,8-diaza-1,2-dithia-6-ethoxycarbonyl-3,3,10,10-tetra-methylcyclodeca-4,8-diene, i.e. Compound 5 of Scheme 1, in 53% yield (1 g), melting point 98°–99° C. IR (thin film) 3450, 1740, 1650 cm$^{-1}$; $^1$H NMR(CDCl$_3$) δ 6.9(m,2,c—N=CH—), 3.0–4.6(m.-5.—OCH$_2$CH$_3$, —NCH$_2$CH—N—), 1.5[m,15,2 >C(CH$_3$)$_2$, —OCH$_2$CH$_3$].

Procedure II

To 1.0 g (5 mmol) of the bisaldehyde 2 in 10 mL of methanol is added dropwise 1.0 g (5 mmol) of the ester 4 and 1 g (12 mmol) of sodium bicarbonate in 20 mL of a 50:50 by volume mixture of methanol and water. The mixture is stirred at 0° C. for 10 minutes, after which time 10 mL of water is added. The resultant mixture is maintained at room temperature,. with stirring, for 2 hours. Water is added until the white precipitate which forms separates out of solution. The precipitate is removed by filtration and taken up in chloroform. Removal of the solvent by rotary evaporation affords 0.4 g (21% yield) of Compound 5, having a melting point and $^1$H NMR spectrum identical to the product of Procedure I.

Procedure III

A solution of 8 g of the ester 4 and 7 mL of pyridine in 200 mL of methanol is added dropwise over a two hour period to a solution of 8 g of bisaldehyde 2 in 25 mL of methanol. The reaction mixture is cooled in an ice bath after the addition for 1 hour, then is allowed to remain at room temperature for 1 hour. The reaction mixture is then placed in a freezer (−20° C.) overnight. The solution is concentrated to one-third volume, water is added and the aqueous solution is extracted with cloroform. The chloroform extract is washed with saturated aqueous sodium chloride solution and dried over magnesium sulfate. Removal of the solvent leaves a viscous mass, which is dissolved in 20 mL of hexane.

The hexane solution is cooled in an acetone/dry ice bath until a white powder separates. The product is removed by filtration and taken up in chloroform. The chloroform solution is concentrated. White crystals of Compound 5 are formed on standing. Yield 7 g. melting point 95°–96° C. NMR and IR as in Procedure I.

EXAMPLE 4

Procedure I

A solution of 5 g of the ester 5 in 20 mL of tetrahydrofuran and 20 mL of aqueous ammonia is stirred at room temperature for 2 hours, after which time it is allowed to stand at room temperature for 24 hours. Removal of solvent leaves a white powder which is removed by filtration. The product, 6-carbamoyl-5,8-diaza-1,2-dithia-3,3,10,10-tetramethylcyclodeca-4,8-diene, i.e. Compound 6- of Scheme 1, is crystallized from a mixture of isopropanol and water. Yield 4 g (88%), melting point 181°–83° C. IR (KBr) 3300, 3100 1650 cm $^{-1}$; $^1$H NMR (CDCl$_3$) δ 7.0(m,2, —HC=N—), 6.4(broad band, 2, —CONH$_2$), 3.8–4.6[m,3,—NCH$_2$—CH(N—)CO—], 1.5, 1 4[s, 12, >C(CH$_3$)$_2$)].

Procedure II

A solution of 5 g of the ester 5 in 20 mL of tetrahydrofuran, 20 mL of ethanol and 20 mL of aqueous ammonia (28%) was stirred at room temperature for 16 hours. Removal of the solvent leaves Compound 6 as a white powder, which crystallizes from toluene as white plates. Yield 4 g, melting point 193°–194° C. IR and NMR as in Procedure I.

EXAMPLE 5

To 3.7 g of the amide 6 in 25 mL of 95% ethanol is added 2 g of sodium borohydride. The mixture is stirred at room temperature for 2 hours, then is heated at reflux for 2 hours. The solution is thereafter concentrated in vacuo and water is added to precipitate the product. The white crystalline product is removed by filtration. Recrystallization from, a mixture of isopropanol and water affords . 6-carbamoyl-5,8-diaza-1,2-dithia-3,3,10,10-tetramethylcyclodecane, i.e. Compound 7 of Scheme 1, as fine white needles melting at 138°–139° C. Yield 3 g. 1H NMR(CDCL$_3$) δ 2.3–4.0[m,7, —NCH$_2$.CH—N—, 2—NCH$_2$—C(CH$_3$)—S—], 1.8(broad band, 2, —CONH$_2$),1.3[m,14, C(CH$_3$)$_2$), —CNH—CH$_2$—].

EXAMPLE 6

A solution of 1.8 g of the amide 7 in 50 mL of dry tetrahydrofuran is added dropwise to a slurry of 1 g of lithium aluminum hydride in 100 mL of dry tetrahydrofuran. The addition takes place over a 30 minute period. The mixture is then heated at the reflux temperature for 20 hours. At the end of that time, the reaction mixture is first cooled and then quenched with saturated Na-K tartrate solution. The aqueous phase is extracted with chloroform. The combined organic phase is then dried over sodium sulfate. Removal of the solvent by rotary evaporation affords, as a viscous oil, 5-aminomethyl-4,7-diaza-2,9-dimethyldecane-2,9-dithiol, i.e. Compound 8 of Scheme 1; $^1$H NMR (CDCl3) δ 2.8[m,9,—NCH$_2$CH—C(CH$_2$)NH—$^{31}$, 2—NCH$_2$—C(CH(hd 3)$_2$S—], 1.5[m,14,, >C(CH$_3$)$_2$, —SH].

EXAMPLE 7

Methoxyamine hydrochloride (5 g; 0.06 mol) is dissolved in 50 mL of methanol and the solution is neutralized to pH 6 with 1 M methanolic KOH. The resultant mixture is filtered and to the filtered solution is added 3.2 g (0.03 mol) of 3-pyridinecarboxaldehyde. That mixture is heated at reflux for 4 hours. The methanol is evaporated and the solid is crystallized from a mixture of ethanol and water. There is thus obtained 0-methyl-3-pyridinealdoxime having the structural formula

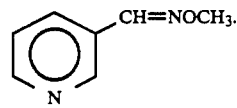

A mixture of 2.7 g (22 mmol) of 0-methyl-3-pyridinealdoxime and 7 g (33 mmol) of 1-chloro-2,4-dinitrobenzene is maintained on a water bath for 1 hour while being stirred to a red homogenous mixture. The resultant mixture is dissolved in 35 mL of methanol, treated with charcoal and filtered. The filtrate is treated successively with two 100 mL portions of ether. The ether mixture is stirred and the product is removed by filtration. Obtained in this manner is 3-[(methoxyimino)-methyl]-1-(2,4-dinitrophenyl)pyridinium chloride, i.e. the Zincke reagent identified as Compound 9 in Schemes 1, 3, 5, 8, 9 and 13.

EXAMPLE 8

A solution of 1.6 g (5 mmol) of the Zincke reagent 9 in 2 mL of methanol is added dropwise to 2.65 g (10 mmol) of the amine 8 in 2 mL of methanol. The reaction mixture is heated at reflux for 2 hours, after which time ether is added to precipitate the product. Alternatively, amine 8 may be utilized as its hydrobromide salt and the reaction may be conducted in the presence of triethylamine (5–10 mmol). There is thus obtained 1-{{2′,3′-bis-{N-[(2″-mercapto-2″-methyl)propyl]amino}propyl}}-3-[(methoxyimino)-methyl]pyridinium chloride, i.e. Compound 10 of Scheme 1.

EXAMPLE 9

To 3.15 g of the dialdehyde 2 is added 4.0 g of ethylenediamine, with stirring and cooling, over a period of 10 minutes. The thick mass which results is stirred for an additional one minute period, then allowed to stand for 1 hour at room temperature and subsequently cooled for 16 hours in a freezer (−20° C.). The solid is removed by filtration and washed with 500 mL of water. The white product is then taken up in chloroform and the chloroform solution is dried over sodium sulfate. Removal of the chloroform gives 2.5 g of 5.8-diaza-1.2-dithia-3,3,10,10-tetramethylcyclodeca-4,8-diene, i.e. Compound 24 of Scheme 3, as a white crystalline product, melting at 168°–170° C. (lit. 162°–164° C., 163°–166° C.). $^1$H NMR(CDCl$_3$) δ 6.9(s,2,—HC=N—), 4.2,3.0(doublet of doublet. 2, 2—CH$_2$—CH$_2$), 1.40[s,6,—C(CH$_3$)$_2$—]Anal. Calcd. for C$_{10}$ C$_{18}$N$_2$S$_2$: C, 52.13; H, 7.88; N, 12.16; S, 27.83. Found: C, 52.20; H, 7.90; N, 12.14; S, 27.74.

EXAMPLE 10

A solution of 0.5 g of 24 and 0.3 g of sodium borohydride in 23 mL of ethanol is stirred- at room temperature for 1 hour, then is heated at the reflux temperature for 20 minutes. Then, 10 mL of water are added and the mixture is heated for an additional 10 minutes. The solvent is partially removed by rotary evaporation and the residue is extracted three times with 10 mL portions of chloroform. The chloroform extract is dried over sodium sulfate and the solvent is removed by rotary evaporation. The resultant liquid solidifies on cooling. Flash chromatography (eluent hexanes/dichloromethane/isopropanol 5:1:1 by volume) gives 5,8-diaza-1,2-dithia-3,3,10,10-tetramethylcyclodecane, i.e. Compound 25 of Scheme 3, as a solid, melting at 52°–53° C. $^1H$ NMR(CDCl$_3$) δ 3–2.1(m,10 ring protons), 1.1,1.2(s,6 CH$_3$, CH$_3$).

EXAMPLE 11

N-(t-butoxycarbonyl), N-(2-mercaptoethyl)glycyl homocysteine thiolactone 67 is prepared as described in Examples 1 and 2 of Byrne et al U.S. Pat. No. 4,434,151, and is dissolved (1.0 gram; 3 millimoles) in 25 milliliters of tetrahydrofuran (THF). The resulting solution is then cooled to about 0° C. and ethylenediamine (1.8 grams; 30 millimoles) is added to form a new solution. The resulting new solution is maintained for about one hour. The volatile components of the solution are thereafter removed with a rotary evaporator. n-Butanol (about 10 milliliters) is added to the "dried" solution components and the liquid components of the resulting composition are again removed by rotary evaporation. The last step is repeated until the vapors remaining in the evaporation vessel do not cause a moistened pH-indicator paper to indicate a basic pH value, thereby also indicating that the ethylenediamine has been substantially removed and that the N-(t-butoxycarbonyl), N-(2-mercaptoethyl)-glycyl N'-(2-aminoethyl)-homocysteinamide, i.e. Compound 68 of Scheme 7, so obtained is substantially pure.

EXAMPLE 12

A mixture of 8 g (66 mmol) of nicotinamide and 20 g (99 mmol) of 1-chloro-2,4-dinitrobenzene is maintained on a water bath for one hour, with stirring. The red homogenous mixture which results is dissolved in 100 mL of methanol and decolorized with charcoal. The filtrate is then treated with 100 mL of ether and the yellow product which separates is removed by filtration and washed with 500 mL of ether. The highly hygroscopic product, 1-(2,4-dinitrophenyl)-3-carbamoyl-pyridinium chloride, is the Zincke reagent 69, employed for example in Scheme 7 and version 3 of Scheme 1. $^1H$ NMR (D$_2$O) δ 8.5–10.0(m,7,ArH,Py-H).

EXAMPLE 13

The procedure of Example 8 is substantially repeated, except that an equivalent quantity of N-(t-butoxycarbonyl), N-(2-mercaptoethyl)glycyl N'-(2-aminoethyl)homocysteine (68) is used in place of the amine 8 and an equivalent quantity of 1-(2,4-dinitrophenyl)-3-carbamoylpyridinium chloride (69) is used in place of the Zincke reagent 9. Obtained in this manner is Compound 70 of Scheme 7.

EXAMPLE 14

Compound 70 (0.002 mol) is dissolved with stirring in absolute ethanol (50 milliliters) and cooled to about 0° C. in an ice-water bath. HCl gas is bubbled through the stirred solution for 15 minutes, and the solution is thereafter stirred for an additional 15 minutes. Diethyl ether (200 milliliters).is thereafter added to the solution to precipitate the salt. The precipitate is filtered and washed with diethyl ether and the solid is then dried in vacuo to provide the corresponding de-protected quaternary, Compound 71 of Scheme 7.

EXAMPLE 15

N-[2-(S-acetamidomethyl)mercaptopropionyl)glycyl homocysteine thiolactone (Compound 77 of Scheme 8). prepared as described in Examples 7 and 9 of Byrne et al U.S. Pat. No. 4,434,151, is suspended (1.0 gram; 3 millimoles) in 25 milliliters of THF. The resulting suspension is cooled to a temperature of about 0° C. in an ice-water bath, and ethylendiamine (1.8 grams; 30 millimoles) is added to form a new solution. N-[2-(acetamidomethyl)mercaptopropionyl]-glycyl N'-(2-aminoethyl)homocysteinamide, i.e. Compound 78 of Scheme 8, is thereafter obtained in a manner substantially similar to that described in Example 11 for the analogous compound.

EXAMPLE 16

The procedure of Example 8 is substantially repeated, except that an equivalent quantity of N-[2-(acetamidomethyl)mercaptopropionyl]glycyl N'-(2-aminoethyl)homocysteinamide (78) is used in place of the amine 8. Obtained in this manner is Compound 79 of Scheme 8.

EXAMPLE 17

1-{{2',3'-bis-{N-[(2''-mercapto-2''-methyl)propyl-]amino}propyl}}-3-[(methyoxyimino)methyl]-pyridinium chloride, i.e. Compound 10 (0.17 mmol), is dissolved in 1.0 mL of absolute ethanol and 1.0 mL of 1N NaOH. A 1.0 mL generator eluant of $^{99m}TcO_4^-$ (5 to 50 milliCuries) in saline is added. Then, 0.5 mL of dithionite solution, prepared by dissolving 336 mg of Na$_2$S$_2$O$_4$ per mL of 1.0 NaOH, is added and the mixture heated sufficiently to reduce both the technetium and the pyridinium salt and to form the complex between the dihydropyridine-containing ligand and the oxotechnate-99m ion. The complex so prepared, i.e. Complex 12 of Scheme 1, is buffered by the addition of 1.0 mL of 1N NaCl and 4.0 mL of 0.1 mL of NaH$_2$PO$_4$, pH 4.5 buffer.

EXAMPLE 18

The generator procedure of Example 17 can be repeated to convert Compound 20 to Complex 22; Compound 28 to Complex 30; Compound 36 to Complex 38; Compound 46 to Complex 48; Compound 50 to Complex 52; Compound 61 to Complex 63; Compound 71 to Complex 73; Compound 79 to Complex 81; Compound 89 to Complex 91; Compound 99 to Complex 101; Compound 110 to Complex 112; Compound 118 to Complex 121; and so forth.

EXAMPLE 19

To a slurry of 11 g of lithium aluminum hydride in 300 mL of dry tetrahydrofuran is added dropwise, over a 2 hour period and under an argon atmosphere, 13 g of the amide 6 in 150 mL of dry tetrahydrofuran. After the addition is complete, the reaction mixture is heated at reflux for 30 hours, then quenched with saturated Na-K tartrate solution. Treatment with 3N hydrochloric acid and then with saturated sodium carbonate solution, followed by filtration and extraction of the filtrate with dichloromethane affords an organic solution which is dried over magnesium sulfate. Removal of the solvent affords the desired amine, Compound 8 of Scheme 1, as a viscous oil.

A sample of the free amine thus obtained is dissolved in diethyl ether and hydrogen chloride gas is added.

The white powder which separates is removed by filtration and purified from ethanol/water to give the corresponding hydrochloride salt melting at 225°–228° C. $^1$H NMR (D$_2$O) δ 3.3–4.2(m,9H,HCl,NH$_2$CH$_2$, —HCl NHCH$_2$), 1.5[m,12H,C(CH$_3$)$_2$]. Anal. Calcd. for C$_{11}$H$_{30}$Cl$_3$N$_3$S$_2$. H$_2$O: C.33.63; H.8.21; N.10.69; Cl,27.07; S.16.32. Found: C,33.93; H,7.94; N,10.60; Cl,27.05; S,16.25.

EXAMPLE 20

A mixture of 1 g of the amine -8, 75 mL of acetone and a catalytic amount of p-toluenesulfonic acid is heated at reflux for 24 hours. The solvent is removed by rotary evaporation and the residue is taken up in chloroform and treated successively with saturated aqueous sodium bicarbonate solution, aqueous sodium hydroxide solution (10%) and saturated aqueous sodium chloride solution. The solution is dried over magnesium sulfate. Removal of the solvent leaves a viscous mass. Thin layer chromatography (CHCl$_3$/methanol, 2:1) indicates two major components having Rf values of 0.13 and 0.73. The component with the lower $R_f$ value shows a positive ninhydrin test, confirming that it is the desired primary amine 8a while the component with the higher $R_f$ value is negative. $^1$H NMR of the Rf 0.73 component (CDCl$_3$): δ 2.9, 2.5, 1.3–1.5. $^1$H NMR of the $R_f$ 0.13 component (CDCl$_3$): δ 3.0, 2.8, 2.3, 1.2–1.7. Obtained in this manner is the desired tisthiazolidine primary amine, Compound 8a of Scheme 1.

EXAMPLE 21

Reaction of the bisthiazolidine primary amine 8a with the Zincke reagent 9 according to the procedure of Example 8 affords the corresponding bisthiazolidine quaternary. i.e. Compound 10a of Scheme 1, which can then be de-protected. e.g. by reaction with mercuric chloride, followed by treatment with hydrogen sulfide, to give the unprotected quaternary. Compound 10 of Scheme 1.

EXAMPLE 22

Reaction of the bisthiazolidine primary amine 8a with the Zincke reagent 69 according to the proCedure of Example 8 affords the corresponding bisthiazolidine quaternary. i.e. Compound 10b of Scheme 1; removal of the protecting groups. e.g. by successive treatments with HgCl$_2$ and H$_2$S, affords the corresponding unprotected quaternary, i.e. Compound 10c of Scheme 1.

EXAMPLE 23

A solution of 7 g (3 mmol) of the ester 5 (prepared, for example, as described in Example 3) in 50 mL of dry tetrahydrofuran is added dropwise over a period of 1 hour to 1.8 g (47 mmol) of lithium aluminum hydride in 200 mL of dry tetrahydrofuran. The mixture is heated at reflux for 16 hours, after which time the reaction is quenched with K—Na tartrate solution. The organic phase is dried over sodium sulfate. Removal of the solvent leaves a yellow viscous mass. Yield 4 g (65%) of the desired alcohol, Compound 18a of Scheme 2. $^1$H NMR (CDCl$_3$) δ 2.2–2.8, 3.5, 2.3, 1.5.

EXAMPLE 24

A solution of 2 g of PBr$_3$ is added at 0° C. to 1 g of the alcohol 18a. The mixture is heated at reflux for 30 minutes, then treated with saturated aqueous sodium bicarbonate solution and extracted with chloroform. The chloroform extract is dried over sodium sulfate. Removal of the solvent in vacuo left the corresponding bromo compound. i.e. Compound 19 of Scheme 2. as a clear viscous mass.

EXAMPLE 25

Following the general procedure of Example 20, but substituting an equivalent quantity of the alcohol 18a in place of the amine 8, affords the bisthiazolidine alcohol. Compound 18b of Scheme 2.

EXAMPLE 26

Reaction of the bisthiazolidine alcohol 18b with PBr$_3$ according to the procedure of Example 24 affords the corresponding bromo compound, i.e. Compound 19a of Scheme 2.

EXAMPLE 27

A solution of 17 mL of 2N lithium borohydride in tetrahydrofuran is added to 300 mL of dry tetrahydrofuran under an argon atmosphere. To that solution are added 10 g (0.035 mol) of the ester 40 in 100 mL of dry tetrahydrofuran. The resultant cloudy solution is heated at reflux for 1.5 hours. The reaction is quenched with water and the organic phase is washed with saturated aqueous sodium chloride solution and dried over magnesium sulfate. Removal of the solvent leaves as a white powder which is very soluble in water, the corresponding primary alcohol, Compound 32 of Scheme 4. Yield 2 g (24%); melting point 85°–90° C.; $^1$H NMR (acetone-d$_6$) δ 7–8, 4.15, 3.3–4.0.

EXAMPLE 28

To 1 g of the alcohol 32 in 40 mL of dry ethanol is added a solution of sodium thiobenzoate prepared from 0.2 g of sodium in 10 mL of ethanol and 1.26 g of thiobenzoic acid in 5 mL of ethanol. The reaction mixture is stirred at room temperature for 10 minutes, then is heated at 45° C. for an additional 10 minutes, The mixture becomes very thick and difficult to stir and a yellow product separates. The product, Compound 33 of Scheme 4, is removed by filtration and washed with water. Yield 1.2 g, melting point 151°–152° C.; $^1$H NMR (DMSO-d$_6$/acetone-d$_6$) δ 7.4–8.3. 3.85. 3.1–3.6.

EXAMPLE 29

To 50 mL of dichloromethane are added 2 9 (4.5 mmol) of the alcohol 33 and 0.35 g (4.5 mmol) of dry pyridine. The solution is cooled and 0.8 g (6.8 mmol) of thionyl chloride in 5 mL of dichloromethane is added dropwise over a ten minute period. The solution is allowed to stir overnight at room temperature. Then an additional 50 mL of dichloromethane is added and the solution is washed successively with 2N hydrochloric acid, saturated sodium bicarbonate solution and water. Drying over magnesium sulfate and removal of the solvent left a yellow solid having an $R_f$ (CH$_2$Cl$_2$/acetone) of 0.47. Yield 1.7 g (81.6%) of the chloro derivative, Compound 34a of Scheme 4, which melts at 129°–131° C.

Chelating agent precursors, chelating agents and radiopharmaceuticals within the purview of the present invention can also be prepared based on the bifunctional chelating agents of Yokoyama et al U.S. Pat. No. 4,287,362. Thus, for example, Yokoyama et al's chelating agents of the formula

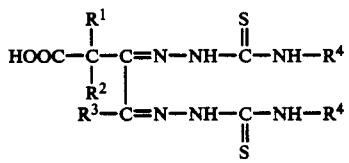

wherein $R^1$, $R_2$, $R_3$ and $R_4$ are each H or $C_1-C_3$ alkyl can be first converted to the corresponding esters (e.g. replacing —COOH with —COOC$_2$H$_5$), which can then be reduced to the corresponding alcohols (replacing —COOC with —CH$_2$OH), which can then be converted to the corresponding —CH$_2$Br or —CH$_2$Cl derivatives, which can in turn be reacted with the selected pyridine compound of the formula

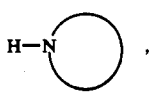

thus replacing the halogen atom to afford quaternary salt of formula (I) herein. Other process variations will be apparent from the many reaction schemes depicted hereinabove.

Another bifunctional chelating agent which can be readily converted to the redox system-containing chelating agent precursors, chelating agents and radiopharmaceuticals of this invention is a compound of the formula

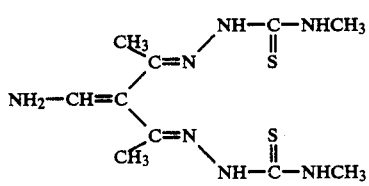

which is also known as amino DTS and which is described in the literature, e.g. in *Jap. J. Nucl. Med.* 19, 610 (1982). Amino DTS can be readily converted to the derivatives of the present invention by reacting it with a Zincke reagent of the formula

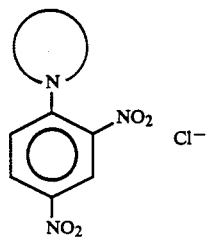

wherein

is as defined with formula (I) hereinabove above to afford the corresponding precursor of formula (I), which can then be utilized as generally described herein to prepare the corresponding compound of formula (II) and radiopharmaceuticals of formulas (III) and (IV). See, for example, Scheme 14 below.

Yet another group of known chelating agents which is particularly well-suited for conversion to the redox system-containing chelating agent precursors, chelating agents and radiopharmaceuticals of the present invention can be represented by the formula

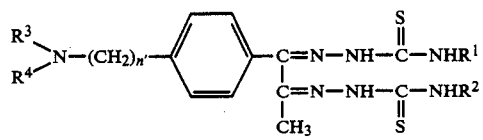

wherein $R_1$, $R_2$, $R_3$ and $R_4$ are each H or $C_1-C_3$ alkyl and n' is an integer of 0 to 3. See, for example, Yokoyama et al U.S. Pat. No. 4,511,550 and Australian Patent No. 533,722. An especially preferred chelating agent encompassed by this group is known as amino-PTS, or AEPM, and has the structure

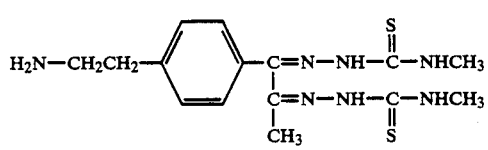

Amino-PTS can be converted to the derivatives of the present invention via a Zincke reagent, as described supra in connection with amino-DTS. See, for example, Scheme 15 below. The exact structure of the resultant technetium complex 136 has not been determined; it is possible that the C=N and C=S bonds are also reduced during one of the reduction steps. One possible structure for 136 is as follows:

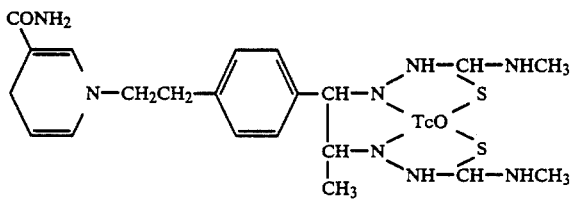

(A similar structure could be depicted for complex 131 of Scheme 14.)

An alternate route to derivatives of amino PTS, amino DTS and the like is depicted in Schemes 16 and 17 below. This route can begin by utilizing known, commercially available pyrylium salts. e.g. Compound 138, to convert the primary amino group of amino PTS, amino DTS or the like into a pyridinium intermediate. The resultant pyridinium intermediate (e.g. 140 or 143) can then undergo nucleophilic displacement to afford the corresponding halo compound (e.g. 141 or 144).

The halo derivative can then be reacted the selected pyridine compound of the formula

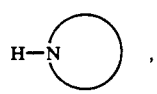

to afford the corresponding quaternary salt of (I) herein, which can be converted to the instant derivatives of formulas (II), (III and (IV) as already described hereinabove.

SCHEME 14

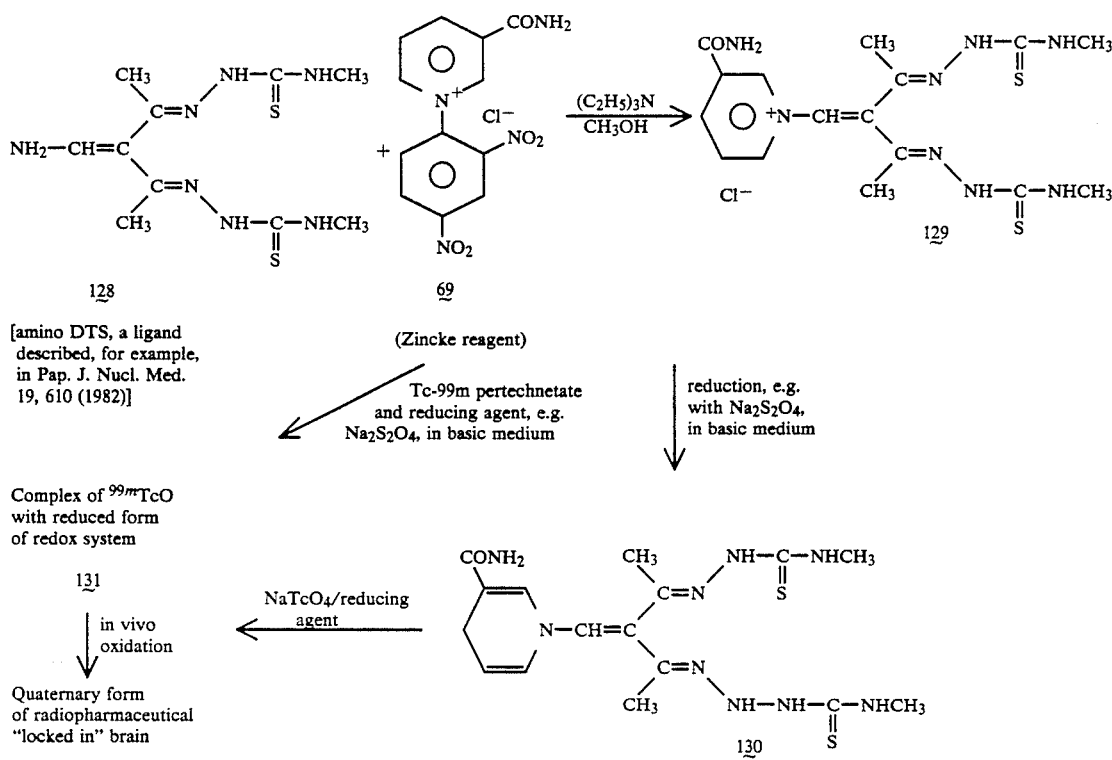

128

[amino DTS, a ligand described, for example, in Pap. J. Nucl. Med. 19, 610 (1982)]

69

(Zincke reagent)

Tc-99m pertechnetate and reducing agent, e.g. $Na_2S_2O_4$, in basic medium reduction, e.g. with $Na_2S_2O_4$, in basic medium Complex of $^{99m}TcO$ with reduced form of redox system

131 in vivo oxidation

Quaternary form of radiopharmaceutical "locked in" brain

132

129

130

SCHEME 15

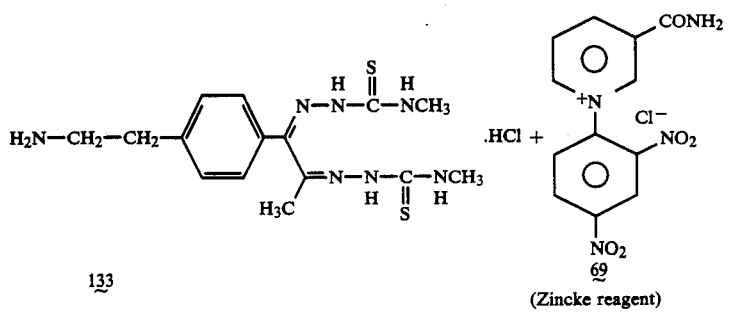

133

(a salt of amino PTS, described for example in Yokoyama et al U.S. Pat. No. 4,511,550 and Austrialian Patent No. 533,722)

69

(Zincke reagent)

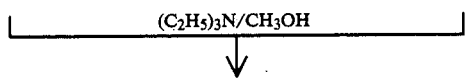

$(C_2H_5)_3N/CH_3OH$

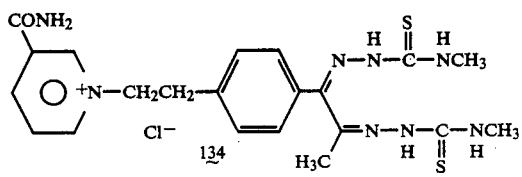

134

Tc-99m pertechnetate and reducing agent, e.g. $Na_2S_2O_4$, in basic medium reduction, e.g. with $Na_2S_2O_4$, in basic medium

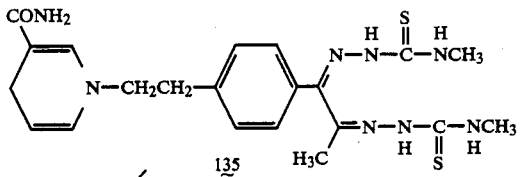

135

Complex of $^{99m}TcO$ with reduced form of redox system $NaTcO_4$/reducing agent

135 in vivo oxidation

Quaternary form of radiopharmaceutical "locked in" brain

137

SCHEME 16
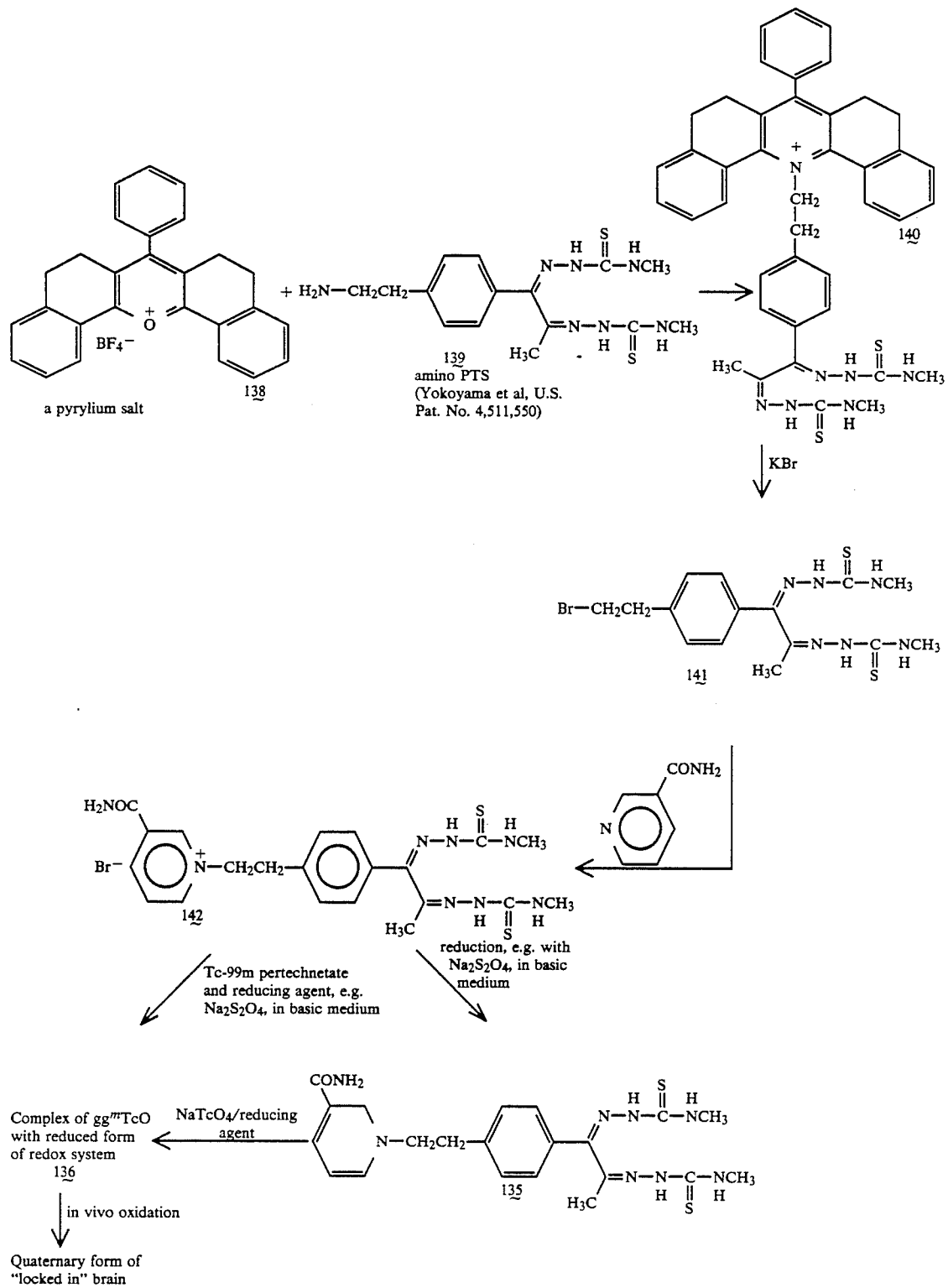

SCHEME 17
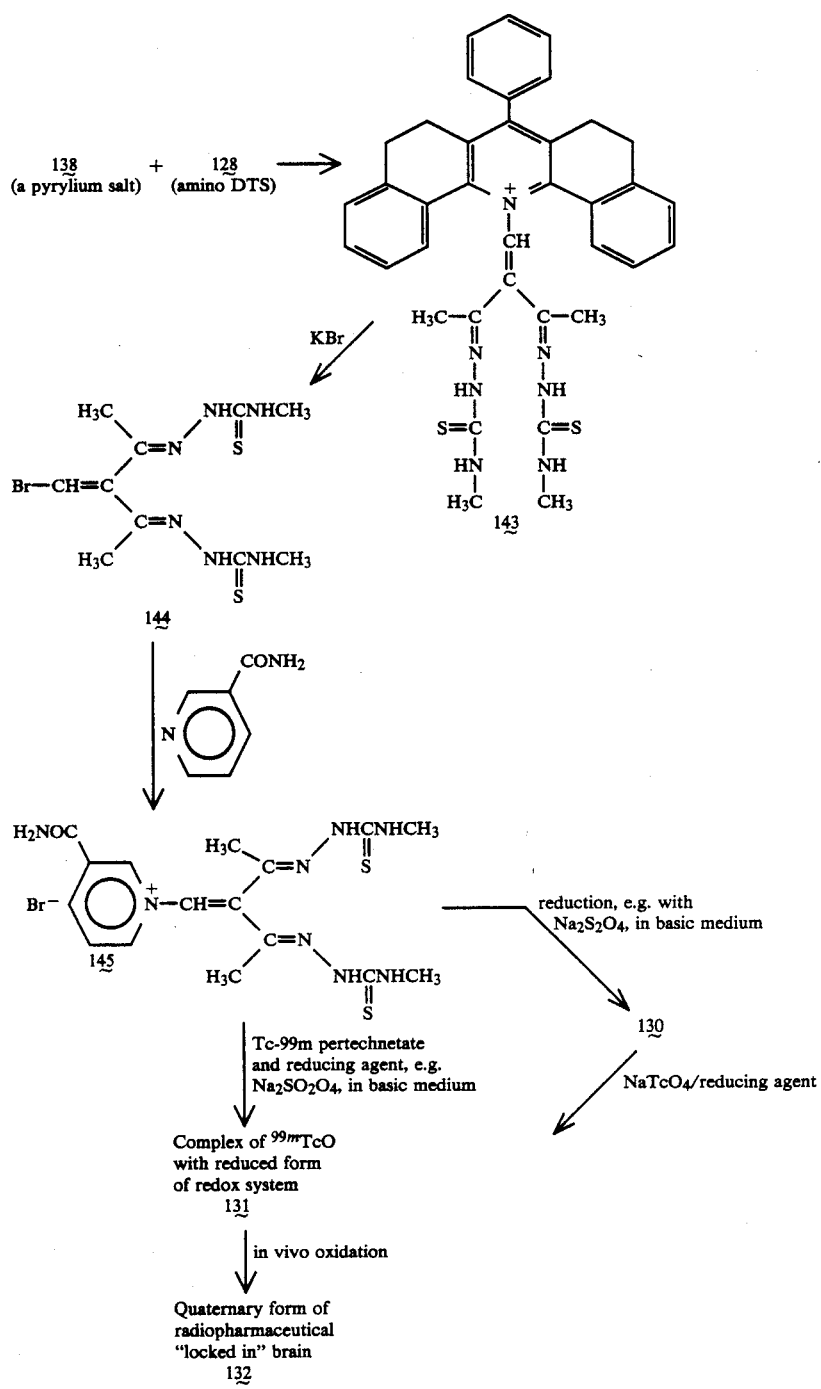
Fritzberg U.S. Pat. No. 4,444,690 describes an interesting series of 2,3-bis(mercaptoalkanoamido)alkanoic acid chelating agents of the general formula
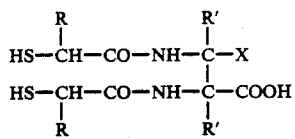
wherein X is H or —COOH, and R and R' are H or lower alkyl, and water-soluble salts thereof, used to prepare the corresponding radiopharmaceuticals of the formula

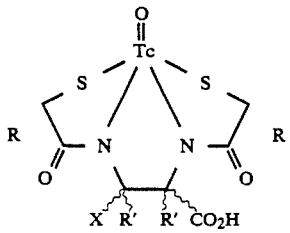

wherein X is H or —COOH, and R and R' are H or lower alkyl. The Fritzberg chelating agents are prepared from the corresponding 2,3-diaminoalkanoic acids by esterification with a lower alkanol containing dry HCl, followed by treating the resultant alkyl ester with a chloroalkanoyl chloride to form the bis(-chloroalkanoamide)ester, followed by treating that ester with

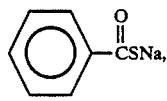

followed by alkaline hydrolysis of the resultant 2,3-bis(-benzoylmercaptoalkanoamido)alkanoic acid ester to produce the 2,3-bis(mercapto-alkanoamido)alkanoic acid chelating agent. Preparation of an analog from 3,4-diaminobenzoic acid is also disclosed by Fritzberg. Many of Fritzberg's synthetic steps can be adapted to produce the formula (I) derivatives of this invention in which, in place of the —COOH group in Fritzberg's chelating agent, there is a

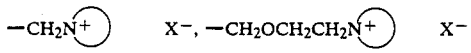

or like group, wherein

and $X^-$ are as defined with formula (I) hereinabove. See, for example, Schemes 4, 5, 6 and 11 hereinabove.

Suitable nontoxic pharmaceutically acceptable diluents or vehicles for use with the present complexes of formula (III) will be apparent to those skilled in this art. See, for example, *Remington's Pharmaceutical Sciences*, 4th Edition (1970). Obviously, the choice of suitable diluents or vehicles will depend upon the exact nature of the particular dosage form selected.

The dosage ranges for administration of the complexes according to this invention will vary with the size and species of the subject, the objective for which the complex is administered, the particular dosage form employed, and the like, as discussed below. The quantity of given dosage form needed to deliver the desired dose of the radiopharmaceutical, of course, depends upon the concentration of the complex in any given pharmaceutical composition/dosage form thereof and the radioactivity thereof.

By way of example only, a 5-50 mg/kg dose of formula (III) radiopharmaceutical, injected into the tail vein or carotid vein of rats, due to the "lock in" mechanism will exhibit a very significant difference between brain and peripheral levels of radioactivity, with consequent ready radioimaging of the brain; imaging at approximately 60 to 90 minutes after administration will be most effective, since it will take advantage of this brain/peripheral differential.

The instant radiopharmaceuticals are generally administered intravenously. Sustained release administration, typically by slow intravenous infusion, will further enhance the site-specificity of the instant redox system. The rate of release of the formula (III) radiopharmaceutical from the sustained release system should be comparable to the rate of in vivo oxidation of the dihydro form (III) to the quaternary form (IV) in order to achieve the greatest degree of enhancement of specificity.

In a further aspect, the present invention also provides a process for the manufacture of a diagnostic agent for the visualization of an organ such as the brain. To that end, the blood-brain barrier- penetrating form, formula (III), is admixed with an aqueous buffer medium having a pH value of about 4 to about 8, preferably of about 6.5 to about 7.5, in an effective radioimaging amount.

Preparation of the radiopharmaceutical can be carried out in the hospital or like location where the patient is found in order to minimize losses of radioactivity caused by the decay of radioactive metal. Inasmuch as the preparation for visualization is injectable, it must be sterile and pyrogen-free; preferably, it is also isotonic. To this end, a so-called labeling kit can be provided that permits a simple, rapid and safe labeling of the solution to be injected with the radioactive metal e.g., technetium-99m. Such kits are especially desirable when a short-lived radioisotope such as technetium-99m is used.

The kit includes a collecting vial for receiving and/or containing an aqueous medium in which the complexing reaction can be effected. Additionally, the kit includes the chelating agent of formula (II) or chelating agent precursor of formula (I) and a pharmacologically acceptable reducing agent for reducing the radioactive element to an appropriate oxidation state for complexing with the chelating agent [and also for reducing the pyridinium moiety to the corresponding dihydropyridine form, when a chelating agent precursor of formula (I) is present].

In the case of technetium-99m, the radioactive element is received from a radionuclide generator as an aqueous pertechnetate ($TcO_4^-$) solution such as an eluate in isotonic saline, as is well-known in the art. The amount of Tc-99m required to produce a quantity of formula (III) radiopharmaceutical sufficient for diagnostic purposes is generally from 0.01 milliCurie (mCi) to about 500 mCi per mL of 99m-pertechnetate solution. The reducing agent for the pertechnetate can be a thiosulfate or dithionite if the reducing reaction is to be carried out in a basic medium, or a tin (II) salt such as $SnCl_2$ if the reducing reaction is to be carried out in an acid medium.

A kit for preparing an injectable radiopharmaceutical, e.g., for complexing an organ-specific agent labeled with a radioactive metal, includes, in separate containers: (1) a biologically compatible, sterile aqueous medium suitable for complex formation with a radioactive metal, (2) a dihydropyridine⇌pyridinium salt redox system-containing complexing agent of formula (I) or (II) compatible therewith, and (3) a pharmaceutically acceptable reducing agent for the radioactive metal.

The dihydropyridine⇌pyridinium salt redox moiety may be present in the kit either in its oxidized or its reduced state, as desired. The reducing agent for the radioactive metal can be selected to reduce also the oxidized form of the redox moiety, if present, as the radioactive metal is reduced to form the complex preparatory to injection of the radiopharmaceutical into a test animal or a patient. In a preferred embodiment of this invention, a reducing agent capable of reducing both the oxidized form of the redox moiety and the radioactive metal is chosen and the chelating agent precursor of formula (I) is present in the kit. In an especially preferred embodiment, the kit comprises, in separate containers (preferebly aseptically and hermetically sealed vials of approximately 5-25 mL volume), (1) a biologically compatible, sterile aqueous medium, (2) a chelating agent precursor of formula (I). and (3) a pharmacologically acceptable reducing agent capable of reducing the chelating agent precursor of formula (I) to a chelating agent of formula (II) and also capable of reducing the radioactive metal to an oxidation state in which it is capable of complexing with the formula (II) chelating agent to form a radiopharmaceutical of formula (III). Most preferably, the reduCing agent is sodium dithionite; also most preferably, the radioactive metal is technetium. The dithionite reduction is preferably carried out in basic medium; this may be accomplished by providing that the aqueous medium (1) above is of basic pH, or by adding an appropriate base (e.g. NaOH, Na$_2$CO$_3$) when combining the kit components and the pertechnetate solution. As yet another alternative, the kit could comprise only two separate components: (1) the biologically compatible, sterile aqueous medium of essentially neutral pH containing the chelating agent precursor of formula (1); and (2) the reducing agent e.g. sodium dithionite or (2) the reducing agent together with the base, e.g. sodium dithionite and sodium carbonate.

Radioactive metal ions are typically not provided with the kit due to the relatively short half-lives of commonly utilized radionuclides. Rather, the radionuclide is provided separately as described earlier and admixed with the components of the kit shortly before use, as is known for other radiopharmaceutical delivery systems. In the case of technetium-99m, the pertechnetate solution and the basic aqueous medium may be first combined and then heated. e.g. from 40° to 95° C. for 10 to 20 minutes. in the presence of the reducing agent, then cooled to about room temperature or below prior to addition of the formula (I) precursor. In this instance, the technetium will be reduced prior to reduction of the quaternary moiety to the corresponding dihydro form, in which case a substantial portion of the quaternary salt (I) will likely chelate with the reduced technetium to form the quaternary complex (IV) in the reaction mixture as an intermediate to the dihydro complex (III), rather than the quaternary salt (I) being first converted to the dihydro chelating agent (II) and then to the dihydro complex (III). Alternatively, if only minimal or no heating is done, the precursor may be present in the initial mixture made from the kit, and it is likely in this instance that the formula (I) quaternary will be first reduced to the formula (II) dihydro, which will then chelate with the reduced technetium to form the complex (III). If the mixture is mildly basic, e.g. pH 8 to 9, it may be administered as is, after the reduction and chelation have occurred to form the formula (III) radiopharmaceutical, or the pH may be adjusted to about 7.

If the mixture is more strongly basic, e.g. pH 13, it is generally desirable to adjust the pH to a slightly alkaline or neutral value.

Whatever the exact configuration of the kit, it is preferable for it to contain excess chelating agent precursor (I) or chelating agent (II) with respect to the radionuclide to be complexed therewith, e.g. a 1:2 molar excess. The reducing agent is present in a large excess with respect to the chelating agent precursor (I), e.g. 1:5 to 1:10. When the chelating agent (II) rather than the precursor (I) is present, then the reducing agent is preferably present in a slight excess with respect to the radionuclide.

To effect visualization, the diagnostic agent is administered to a patient, typically intravenously, with or without further dilution by a carrier vehicle such as physiological saline, phosphate-buffered saline, plasma, or the like. Generally, the unit dose to be administered has a radioactivity of about 0.01 milliCurie (mCi) to about 100 milliCuries, preferably about 1 mCi to about 20 mCi. The solution to be injected into an adult patient per unit dosage is about 0.01 milliliter (mL) to about 1 milliliter.

After intravenous administration, imaging of the organ in vivo can take place after a few minutes. If desired, imaging can also take place hours after the injection, depending upon the half-life of the radioactive material that has been introduced into the patient and upon the amount of such material introduced. Preferably, imaging takes place 60 to 90 minutes after intravenous administration.

Any conventional method of imaging for diagnostic purposes can be utilized when practicing the present invention.

In summary, then, in its broadest aspects the present invention can be seen to provide compositions of matter comprising: (1) the residue of a chelating agent having at least one primary, secondary or tertiary amino functional group, said functional group being not essential for the complexing properties of said chelating agent, said residue being characterized by the absence of at least one of said primary, secondary or tertiary amino functional groups, said chelating agent being either (a) capable of chelating with a metallic radionuclide or (b) chelated with a metallic radionuclide; and (2) a dihydropyridine⇌pyridinium salt redox system, which in its oxidized form comprises a radical of the formula

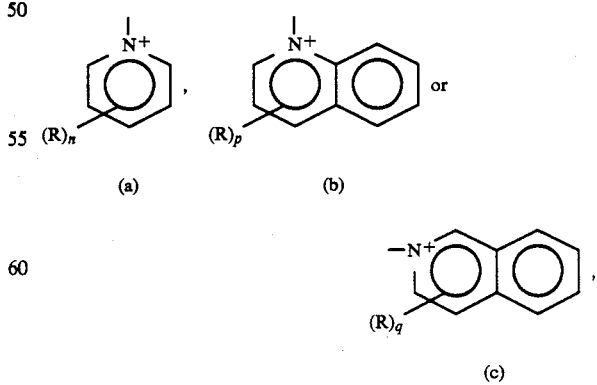

wherein, n, p, q, and R are as defined with formula (I) hereinabove, and which in its reduced form comprises a radical of the formula

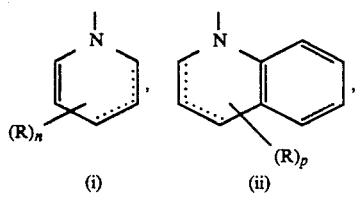

(i)   (ii)

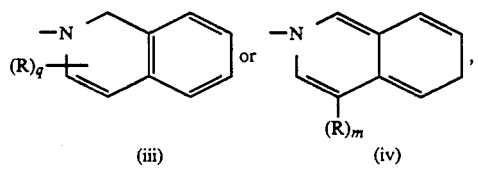

(iii)   or   (iv)

wherein n, p, q, m and R are as defined with formula (II) hereinabove; said redox system being directly attached to said chelating agent residue, the ring nitrogen atom of said redox system occupying the same position relative to said chelating agent residue as the position occupied by said primary, secondary or tertiary amino functional group in said chelating agent.

While the invention has been described in terms of various preferred embodiments, the skilled artisan will appreciate that various modifications, substitutions, omissions, and changes may be made without departing from the spirit thereof. Accordingly, it is intended that the scope of the present invention be limited solely by the scope of the following claims.

What we claim is:

1. A compound having the structural formula

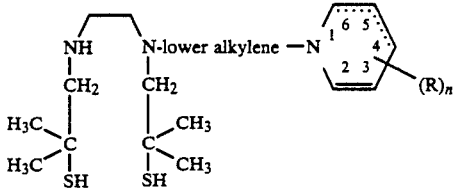

wherein the dotted line indicates the presence of a double bond in either the 4 or 5 position of the dihydropyridine ring; n is zero, one or two; and each R is independently selected from the group consisting of halo, $C_1$-$C_7$ alkyl, $C_1$-$C_7$ alkoxy, $C_2$-$C_8$ alkoxycarbonyl, $C_2$-$C_8$ alkanoyloxy, $C_1$-$C_7$ haloalkyl, $C_1$-$C_7$ alkylthio, $C_1$-$C_7$ alkylsulfinyl, $C_1$-$C_7$ alkylsulfonyl, —CH=NOR''' wherein R''' is H or $C_1$-$C_7$ alkyl, and —CONR'R'' wherein R' and R'', which can be the same or different, are each H or $C_1$-$C_7$ alkyl.

2. A compound as defined by claim 1, wherein n is one.

3. A compound as defined by claim 2, wherein R is located in the 3 position of the dihydropyridine ring.

4. A compound as defined by claim 2, wherein R is —CH=NOR''' wherein R''' is H or $C_1$-$C_7$ alkyl, or wherein R is —CONR'R'' wherein R' and R'', which can be the same or different, are each H or $C_1$-$C_7$ alkyl.

5. A compound as defined by claim 3, wherein R is —CH=NOR''' wherein R''' is H or $C_1$-$C_7$ alkyl, or wherein R is —CONR'R'' wherein R' and R'', which can be the same or different, are each H or $C_1$-$C_7$ alkyl.

6. A compound as defined by claim 5, wherein the dotted line indicates the presence of a double bond in the 4 position of the dihydropyridine ring.

7. A compound having the structural formula

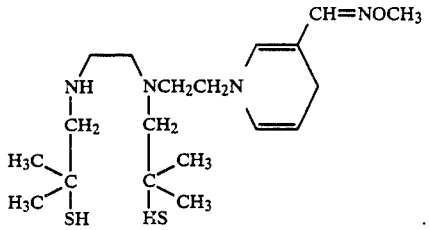

* * * * *